United States Patent
Häsler et al.

(10) Patent No.: US 10,435,474 B2
(45) Date of Patent: Oct. 8, 2019

(54) BAFF SELECTIVE BINDING COMPOUNDS AND RELATED METHODS

(71) Applicant: Ossianix, Inc., Philadelphia, PA (US)

(72) Inventors: Julien Häsler, Hitchin (GB); Julia Lynn Rutkowski, Bryn Mawr, PA (US)

(73) Assignee: Ossianix, Inc., Philadelphia, PA (US)

( * ) Notice: Subject to any disclaimer, the term of this patent is extended or adjusted under 35 U.S.C. 154(b) by 106 days.

(21) Appl. No.: 15/107,921

(22) PCT Filed: Dec. 22, 2014

(86) PCT No.: PCT/US2014/071913
§ 371 (c)(1),
(2) Date: Jun. 24, 2016

(87) PCT Pub. No.: WO2015/100246
PCT Pub. Date: Jul. 2, 2015

(65) Prior Publication Data
US 2016/0333103 A1    Nov. 17, 2016

Related U.S. Application Data

(60) Provisional application No. 61/920,591, filed on Dec. 24, 2013.

(51) Int. Cl.
| | |
|---|---|
| *C07K 16/24* | (2006.01) |
| *A61K 39/395* | (2006.01) |
| *C07K 16/28* | (2006.01) |
| *G01N 33/68* | (2006.01) |
| *A61K 47/68* | (2017.01) |
| *C07K 14/525* | (2006.01) |
| *C07K 14/705* | (2006.01) |
| *C07K 14/71* | (2006.01) |
| *A61K 39/00* | (2006.01) |

(52) U.S. Cl.
CPC ...... *C07K 16/2875* (2013.01); *A61K 39/3955* (2013.01); *A61K 47/6849* (2017.08); *C07K 16/241* (2013.01); *G01N 33/6872* (2013.01); *A61K 2039/505* (2013.01); *C07K 2317/20* (2013.01); *C07K 2317/22* (2013.01); *C07K 2317/565* (2013.01); *C07K 2317/567* (2013.01); *C07K 2317/569* (2013.01); *C07K 2317/76* (2013.01); *C07K 2317/92* (2013.01)

(58) Field of Classification Search
CPC .......... C07K 2317/569; C07K 2317/76; C07K 2317/565; C07K 16/22; C07K 16/24; A61K 39/3955; A61K 39/395; A61K 2039/505
See application file for complete search history.

(56) References Cited

U.S. PATENT DOCUMENTS

2017/0198281 A1    7/2017  Hasler et al.

FOREIGN PATENT DOCUMENTS

| WO | WO2000043032 A2 | 7/2000 |
|---|---|---|
| WO | WO2001012812 A2 | 2/2001 |
| WO | WO2001060397 A1 | 8/2001 |
| WO | WO2002024909 A2 | 3/2002 |
| WO | WO2003014161 A2 | 2/2003 |
| WO | WO2003016468 A2 | 2/2003 |
| WO | WO2005118629 A1 | 12/2005 |
| WO | WO2006025345 A1 | 3/2006 |
| WO | WO2006068867 A1 | 6/2006 |
| WO | WO2006073941 A2 | 7/2006 |
| WO | WO2007140371 A2 | 12/2007 |
| WO | WO2010007082 A1 | 1/2010 |
| WO | WO2011160086 A2 | 12/2011 |

OTHER PUBLICATIONS

Aires da Silva et al. Recombinant antibodies as therapeutic agents. Biodrugs 22(5): 301-314, 2008.*
Barelle et al. VNARs: an ancient and unique repertoire of molecules that deliver small, soluble, stable and high affinity binders of proteins. Antibodies 4: 240-258, 2015.*
Hasler et al. VNAR single-domain antibodies specific for BAFF inhibit B cell development by molecular mimicry. Mol Immunol 75: 28-37, 2016.*
Konning et al. Camelid and shark single domain antibodies: structural features and therapeutic potential. Curr Opin Struct Biol 45: 10-16, 2017.*
Kovaleva et al. Shark variable new antigen receptor biologics—a novel technology platform for therapeutic drug development. Exp Opin Biol Ther 14(10): 1527-1539, 2014.*
Mackay et al. B cells and the BAFF/APRIL axis: fast-forward on autoimmunity and signaling. Curr Opin Immunol 19: 237-336, 2007.*
Rickert et al. Signaling by the tumor necrosis factor receptor superfamily in B-cell biology and disease. Immunol Rev 244: 115-133, 2011.*

(Continued)

*Primary Examiner* — Bridget E Bunner
(74) *Attorney, Agent, or Firm* — Wilson IP Law BA Ruskin Law, LLC

(57) ABSTRACT

The present invention relates to peptide antagonists that bind with high specificity and affinity to B-Lymphocyte stimulator ("BAFF"), thereby antagonizing BAFF receptor ("BAFF-R") signaling. The invention more specifically relates to VNAR single chain antibodies derived from nurse shark that bind to BAFF, BAFF antagonist compounds and compositions comprising a BAFF specific VNAR binding moiety, methods for preparing them, diagnostic and therapeutic methods of use relating to in vitro or in vivo B cell depletion, e.g., to treat and/or prevent a pathological condition, disorder or disease in which it is beneficial to kill or deplete B cells, such as in autoimmune diseases including systemic lupus erythematosus (SLE), rheumatoid arthritis (RA) or multiple sclerosis (MS), and in certain hematological cancers, including lymphomas, leukemias and myelomas.

18 Claims, 18 Drawing Sheets

Specification includes a Sequence Listing.

(56) References Cited

OTHER PUBLICATIONS

Zielonka et al. The shark strikes twice: hypervariable loop 2 of shark IgNAR antibody variable domains and its potential to function as an autonomous paratope. Mar Biotechnol 17: 386-392, 2015.*

Zielonka et al. Structural insights and biomedical potential of igNAR scaffolds. mAbs 7(1): 15-25, 2015.*

Baker et al (2003), "Generation and characterization of LymphoStat-B, a human monoclonal antibody that antagonizes the bioactivities of B lymphocyte stimulator", Arthritis & Rheumatism, Wiley, US, vol. 48, No. 11, pp. 3253-3265.

Diaz et al. (2002), "Structural analysis, selection, and ontogeny of the shark new antigen receptor (IgNAR): identification of a new locus preferentially expressed in early development", Immunogenetics, vol. 54, pp. 501-512.

Fennell et al. (2010), "Dissection of the IgNAR V domain: molecular scanning and orthologue database mining define novel IgNAR hallmarks and affinity maturation mechanisms", J Mol Biol., vol. 400, pp. 155-170.

Gordon et al. (2003), "BAFF/BLyS receptor 3 comprises a minimal TNF receptor-like module that encodes a highly focused ligand-binding site", Biochemistry, vol. 42, No. 20, pp. 5977-5983.

Ju et al. (2007), "Unexpected development of autoimmunity in BAFF-R-mutant MRL-lpr mice", Immunol., vol. 120, No. 2, pp. 281-289.

Kikly et al. (2009), "Characterization of LY2127399; A Neutralizing Antibody for BAFF", Arthritis & Rheumatism; The 2009 ACR/ARHP Annual Scientific Meeting; Philadelphia; Oct. 16-21, 2009, Wiley, US, vol. 60, No. suppl. 10, pp. 1-2.

Liu et al. (2005), "Generation and Characterization of C305, a Murine Neutralizing scFv Antibody That Can Inhibit BLyS Binding to its Receptor BCMA", ACTA Biochimica Et Biophysica Sinica, vol. 37, No. 6, pp. 415-420.

Muller et al. (2012), "Generation and isolation of target-specific single-domain antibodies from shark immune repertoires", Methods Mol Biol., vol. 907, pp. 177-194.

Neri et al (2007), "Neutralizing B-Cell Activating Factor Antibody Improves Survival and Inhibits Osteoclastogenesis in a Severe Combined Immunodeficient Human Multiple Myeloma Model", Clinical Cancer Research, vol. 13, No. 19, pp. 5903-5909.

Ng et al. (2004), "B Cell-Activating Factor Belonging to the TNF Family (BAFF)-R is the Principal BAFF Receptor Facilitating BAFF Costimulation of Circulating T and B Cells", J Immunol, (2004), vol. 173, pp. 807-817.

* cited by examiner

BAFF SELECTIVE BINDING COMPOUNDS AND RELATED METHODS

CROSS REFERENCE TO RELATED APPLICATION

This application is a national stage filing under 35 U.S. § 371 of Intl. Appln. No. PCT/US2014/071913, filed Dec. 22, 2014, which claims the benefits of U.S. Application Ser. No. 61/920,591, filed on Dec. 24, 2013, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 18, 2014, is named OSX1301-WO1_SL.txt and is 52,715 bytes in size.

FIELD OF THE INVENTION

The present invention relates to peptide antagonists that bind with high specificity and affinity to B-Lymphocyte stimulator ("BAFF"), thereby antagonizing BAFF receptor ("BAFF-R") signaling. The invention more specifically relates to VNAR single chain antibodies derived from nurse shark that bind to BAFF, BAFF antagonist compounds and compositions comprising a BAFF specific VNAR binding moiety, methods for preparing them, diagnostic and therapeutic methods of use relating to in vitro or in vivo B cell depletion, e.g., to treat and/or prevent a pathological condition, disorder or disease in which it is beneficial to kill or deplete B cells, such as in autoimmune diseases including systemic lupus erythematosus (SLE), rheumatoid arthritis (RA) or multiple sclerosis (MS), and in certain hematological cancers, including lymphomas, leukemias and myelomas.

BACKGROUND OF THE INVENTION

BAFF-R (also called BR3, TNFRSF13C or CD268) is a tumor necrosis factor (TNF) receptor superfamily member expressed predominantly on mature B-lymphocytes and on a subset of T-cells (L. G. Ng, et al., *J Immunol*, 173 (2004), pp. 807-817. BAFF-R and two other TNF superfamily receptors called TACI (transmembrane activator and calcium modulator and cyclophilin ligand interactor) and BCMA (B-cell maturation antigen), are expressed mainly on B lymphocytes and their expression varies as a function of B cell maturation. Each specifically binds a ligand called B-Lymphocyte stimulator (BAFF; also referred to as BLyS, CD257, TALL-1, THANK, TNFSF13B or ZTNF4) which is expressed in myeloid cells and a variety of other cell types. While BCMA and TACI also interact with other ligands, BAFF-R is reportedly exclusive to BAFF. Each of the three TNF receptors has a different binding affinity for BAFF. BAFF trimerizes and binds to cell surface BAFF-R, upon which the complex is internalized by receptor-mediated endocytosis.

The BAFF/BAFF-R interaction has been shown to be significant in B-cell survival, maintenance and proliferation. Functionally, the BAFF/BAFF-R interaction is critical for maturation of immature transitional B-cells and for survival, migration and activation of mature B-cells including isotype class switching. BAFF can act alone or in concert with other agents, e.g., B-cell receptor (BCR), interleukin-4, interleukin-21 or CD40 ligand.

BAFF antagonists may have therapeutic benefit for treating autoimmune diseases in which B cells play a pathogenic role. Overproduction of BAFF can trigger severe autoimmune disorders in mice resembling systemic lupus erythematosus (SLE) and Sjogren's syndrome (SS) (Ju et al., *Immunol.* 2007 120(2):281-9). Increased levels of BAFF are also found in human patients suffering from SLE, SS, rheumatoid arthritis (RA), Wegener's granulomatosis and certain B-cell malignancies. Moreover, in animal models of autoimmune disease, such as SLE, rheumatoid arthritis (e.g., collagen-induced arthritis) and multiple sclerosis (e.g., experimental autoimmune encephalomyelitis), the disease phenotype can be partially reverted by treating with soluble BAFF-R-Fc fusion proteins that bind to BAFF thereby antagonizing BAFF/BAFF-R interaction. Treatment with BAFF-R-Fc fusion proteins has also been shown to inhibit chronic graft-versus-host disease (cGVHD) by blocking B-cell survival. And, anti-BAFF antibodies are clinically beneficial when administered to rheumatoid arthritis or SLE patients, establishing a nexus between BAFF antagonism and therapeutic efficacy in these autoimmune disorders.

A variety of B-cell malignancies show increased expression of BAFF-R. Different Non-Hodgkin's Lymphoma (NHL) cell lines, for example, express BAFF-R to different degrees. The BAFF/BAFF-R interaction also increases the survival and proliferation of malignant cells, enabling cancer cells to proliferate faster than normal B-cells. Because BAFF-R is thought to be the only receptor that mediates the B cell survival signal from BAFF, agents that modulate BAFF/BAFF-R interaction could be useful treatments for various B cell malignancies.

Accordingly, BAFF-R, as the predominant BAFF receptor expressed on B cell lines, is thought to represent an attractive target for therapeutic intervention in B cell malignancies such as lymphomas and in autoimmune diseases involving B cells. To that end, a number of B-cell targeting therapeutic antibodies have been developed, the earliest ones directed to CD20 (e.g., rituximab, a chimeric mouse/human IgG1 approved for hematological cancers and refractory RA; ofatumumab, a human IgG1 approved for refractory chronic lymphocytic leukemia "CLL" and in clinical trials for other hematological cancers, including relapsing remitting multiple sclerosis "RRMS"; and ocrelizumab, a humanized IgG1 in clinical trials for RRMS). Epratuzumab is a humanized mouse monoclonal antibody directed to CD22, currently in clinical trials for systemic lupus erythematosus "SLE" and Non-Hodgkin's Lymphoma "NHL". Certain human anti-BAFF antibodies have been developed, including belimumab (human IgG1) and blisibimod (human IgG4), which are approved and/or in clinical trials for treatment of SLE and various other indications. See, e.g., WO2011/160086; WO2006/025345; WO2003/016468; and WO2000/043032.

Monoclonal antibodies have revolutionized biotechnology and are now key therapeutic drugs in the treatment of human disease. Despite their successes, therapeutic monoclonal antibodies have certain limitations, such as restricted activity against certain types of antigen, poor tissue penetration, unwanted effector function in many situations, the cost of manufacturing, product instability and aggregation. Single domain antibodies that occur naturally in the shark are particularly attractive for the development of next generation biotherapeutics. VNARs are small (12 kDa), stable, soluble, monomeric antigen-binding domains that can be configured into many different therapeutic modalities. The isolation of various VNAR based binding moieties has been described. See, e.g., WO2003/014161 and WO2005/118629.

It would be desirable to have additional BAFF antagonists, especially ones having one or more advantageous biological properties with therapeutic and/or diagnostic benefit over current anti-BAFF antibodies.

SUMMARY OF THE INVENTION

Complex phage libraries have been generated using a shark VNAR derived scaffold which enables the generation of novel therapeutic products, in particular, specific binding moieties which bind selectively and with high affinity to human BAFF antigen, thereby producing a BAFF antagonist compound. The invention thus provides BAFF specific binding moieties and BAFF antagonist compounds comprising them. BAFF specific binding moieties comprise a CDR1 region and a CDR3 region interspersed by a framework region FW2-3. CDR1 and CDR3 regions are also bordered by framework regions FW1 and FW4, respectively. The CDR1 region comprises or consists essentially of a peptide having an amino acid sequence of formula $D-X_2-X_3-X_4-A-L-X_7$ (SEQ ID NO: 1) in which $X_2$ is N or S; $X_3$ is N, I or S; $X_4$ is C or Y; and $X_7$ is S, P or G. The CDR3 region comprises or consists essentially of a peptide having an amino acid sequence of formula (a) $D-X_a-L-Z_{(1-6)}-C$ (SEQ ID NO: 2) or formula (b) $C-Z_{(1-6)}-D-X_a-L$ (SEQ ID NO: 3) in which $X_a$ is selected from W, P, R, V or L; and $Z_{(1-6)}$ is a stretch of any one to six amino acid residues. Specific framework and CDR region amino acid sequences are provided, and compounds comprising combinations of each region are included. BAFF antagonist compounds compete with or inhibit one or more bioactivities of a native BAFF ligand in vitro or in vivo. Nucleic acid sequences encoding one or more BAFF specific binding moieties, vectors comprising nucleic acid sequences, and host cells comprising them are also provided, as are related methods for producing a BAFF antagonist compound.

BAFF specific binding moieties or BAFF antagonist compounds may be used to produce variants and derivatives, including conjugates, e.g., immunoconjugates. The antagonist compounds, and variants or derivatives thereof, may be combined with other therapeutic agents in compositions for use in related therapeutic, prophylactic and diagnostic methods. Therapeutic methods are provided for treating a B cell related condition, disease or disorder associated with a pathology in B cell proliferation, maturation or maintenance; immunoglobulin production, such as a B cell malignancy or a B-cell related autoimmune condition. Methods for identifying, quantifying or localizing a BAFF-R containing biological sample are also provided, as are methods for the targeted delivery of a payload to a BAFF-R expressing cell using a BAFF specific binding moiety-payload conjugate.

BRIEF DESCRIPTION OF THE DRAWINGS

FIG. 1 discloses SEQ ID NOS 43-53, respectively, in order of appearance.

FIG. 3 discloses the left peptide as SEQ ID NO: 54 and the right side peptides as SEQ ID NOS 57, 57, 58, 58, 59 and 59, respectively, in order of appearance.

FIG. 4 discloses SEQ ID NOS 60-65, respectively, in order of appearance.

DETAILED DESCRIPTION OF THE INVENTION

Figure 1:
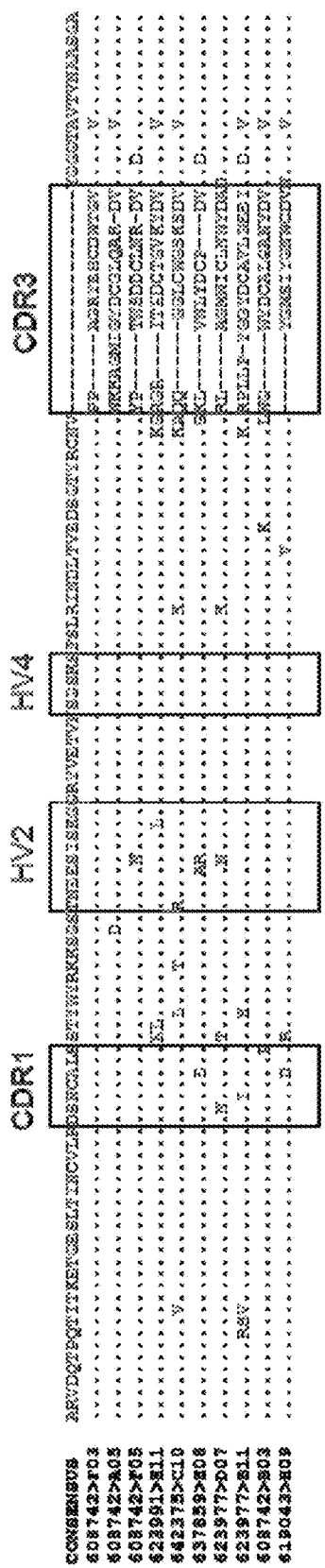
FIG. 1 shows the protein sequence of the ten templates used in the shark library design. The mutations are highlighted.

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

As used herein, the term "BAFF-R" or "BAFF receptor" refers to a mammalian BAFF-R, unless the context indicates that it refers specifically to human BAFF-R, as disclosed in, e.g., WO2000/04032, WO2001/012812, WO2001/060397 and WO2002/024909. WO2006/073941 and WO2010/007082 refer to anti-BAFF-R antibodies in general. WO2006/073941 describes specific anti-BAFF-R antibodies.

VNAR Semi-Synthetic Library Construction and Screening

A Type 2 nurse shark VNAR semi-synthetic library was constructed by a rationale design based on sequence analysis of 189 Type 2 VNAR sequences containing a single cysteine in their CDR3 region (see M. Diaz, et al., *Immunogenetics* 54 (2002) pp. 501-512). These sequences were obtained by randomly sequencing clones in naïve VNAR libraries built from two different adult nurse sharks. Information obtained by alignment of the 189 protein sequences was used to design a new semi-synthetic library including sequence variation in both the CDR3 and the framework regions.

The collected information included:
  (i) The length of the CDR3s: It was observed that more than 80% of the naturally occurring type 2 CDR3s have a length ranging from 11 to 18 amino acids. These 8 different lengths were therefore chosen to build the semi-synthetic library.
  (ii) The position of the single cysteine in the CDR3: The amino acid composition at each position of the CDR3 was analysed and the preferred position of the single cysteine determined in the 8 selected CDR3 lengths. This information was incorporated in the library design by either fixing a single cysteine residue in the CDR3 (using a TGC codon), or by using a "loose" cysteine approach by which the preferred cysteine position, as well as the two immediately adjacent residues, were mutated to a DRY degenerate codon (⅙ chance to form a cysteine).

(iii) The presence of fixed residues in CDR3: The same sequence analysis revealed that the amino acids DV were predominantly found at the last two positions of the CDR3. This sequence information was incorporated into the library design by fixing these two amino acids residues.

(iv) The most commonly found mutations in the framework regions: The analysis of the amino acid composition of the 189 VNAR backbones allowed identification of the most frequently found amino acid substitutions at every position of the framework regions. The most frequent mutations were then introduced in the library design using a mixture of ten selected framework templates accumulating a number of frequently found mutations (FIG. 1) in the PCR reaction.

(v) The sequence conservation on the edges of the CDR3: The same framework analysis allowed identification of specific sequence variations on the edges of the CDR3 region. It was observed that shorter CDR3s (less than 16 amino acids) were usually preceded by the CNV sequence, while longer CDR3s (more than 16 amino acids) were usually preceded by the CKV sequence. This sequence variation was therefore incorporated in the library design by fixing amino acids at these positions. Three main sequence permutations were also observed in C-terminus of the CDR3. These sequence variations were also included in the library design by synthesising three sets of oligonucleotides incorporating each amino acid permutation.

Figure 2:
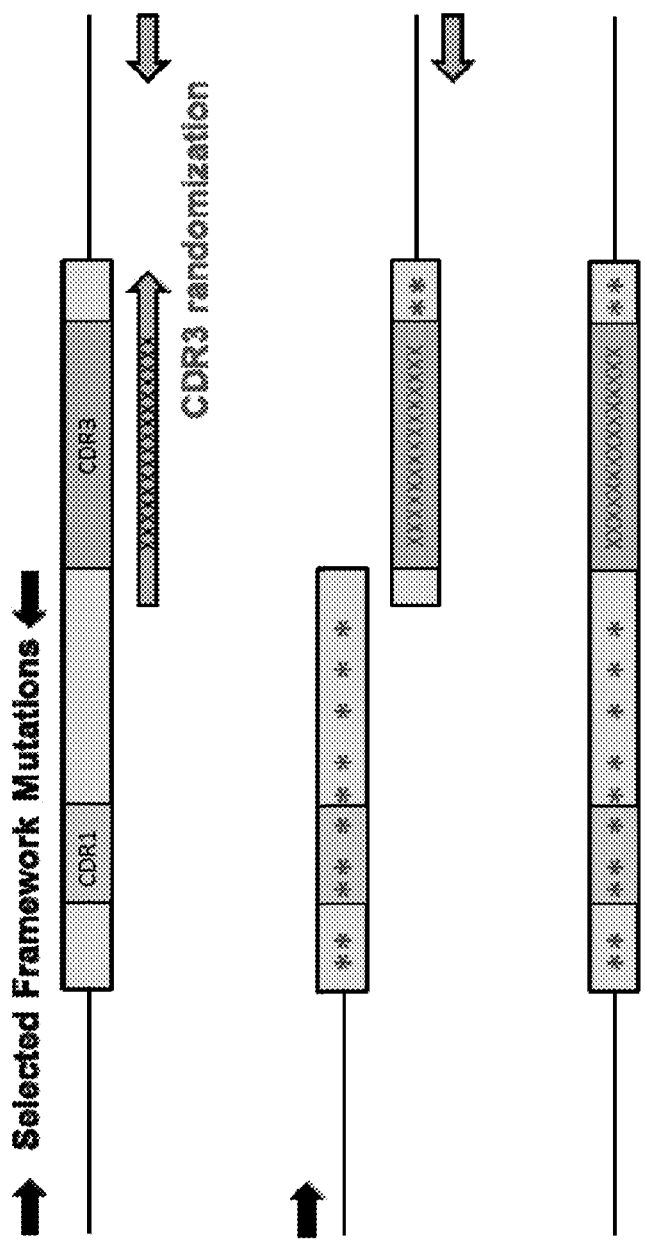
FIG. 2 is a schematic of the overlap PCR principle, in which sequence variability is introduced in both the VNAR frameworks and the CDR3.
Figure 3:
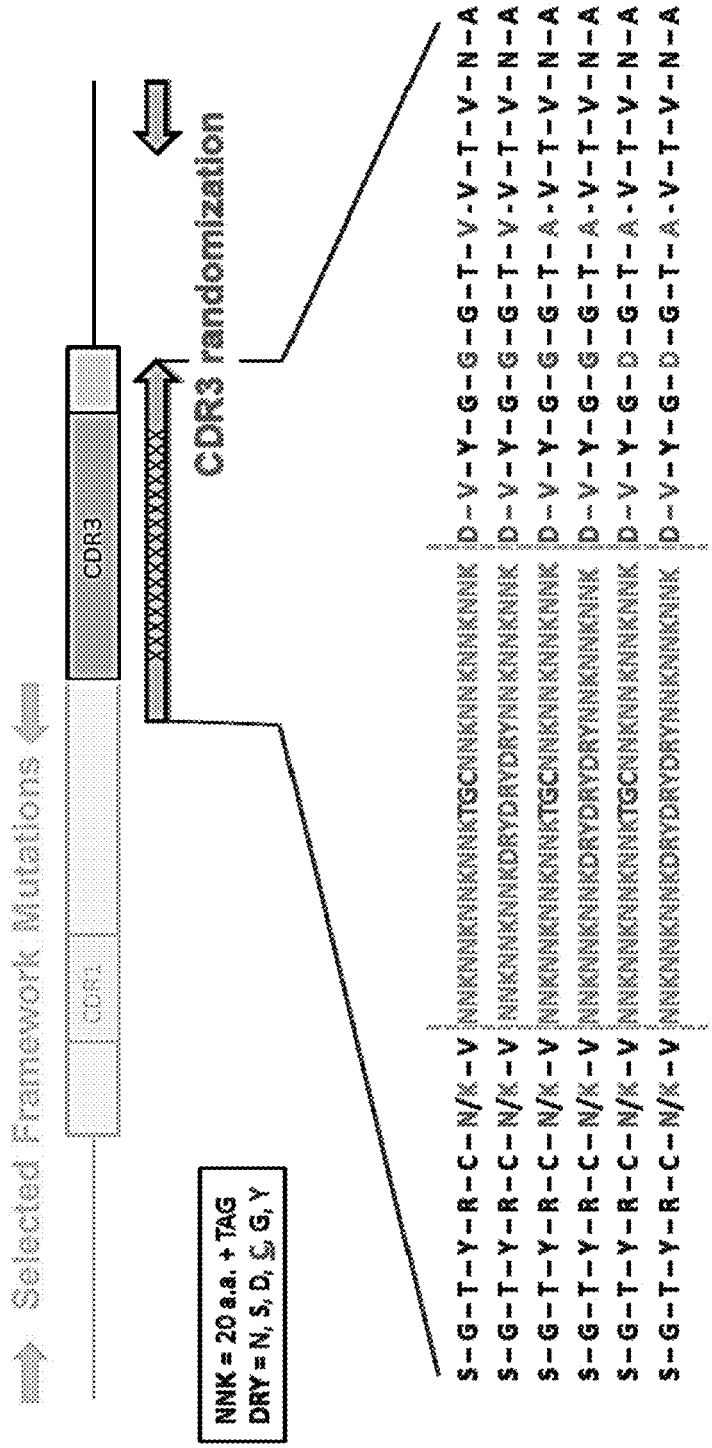
FIG. 3 shows the generic oligonucleotide design used in the library building. A set of six oligonucleotides (SEQ ID NOS 55, 56, 55, 56, 55 and 56 respectively, in order of appearance) was used for each CDR3 length in order to cover all sequence permutations on the edges of the CDR3.
Figure 4:
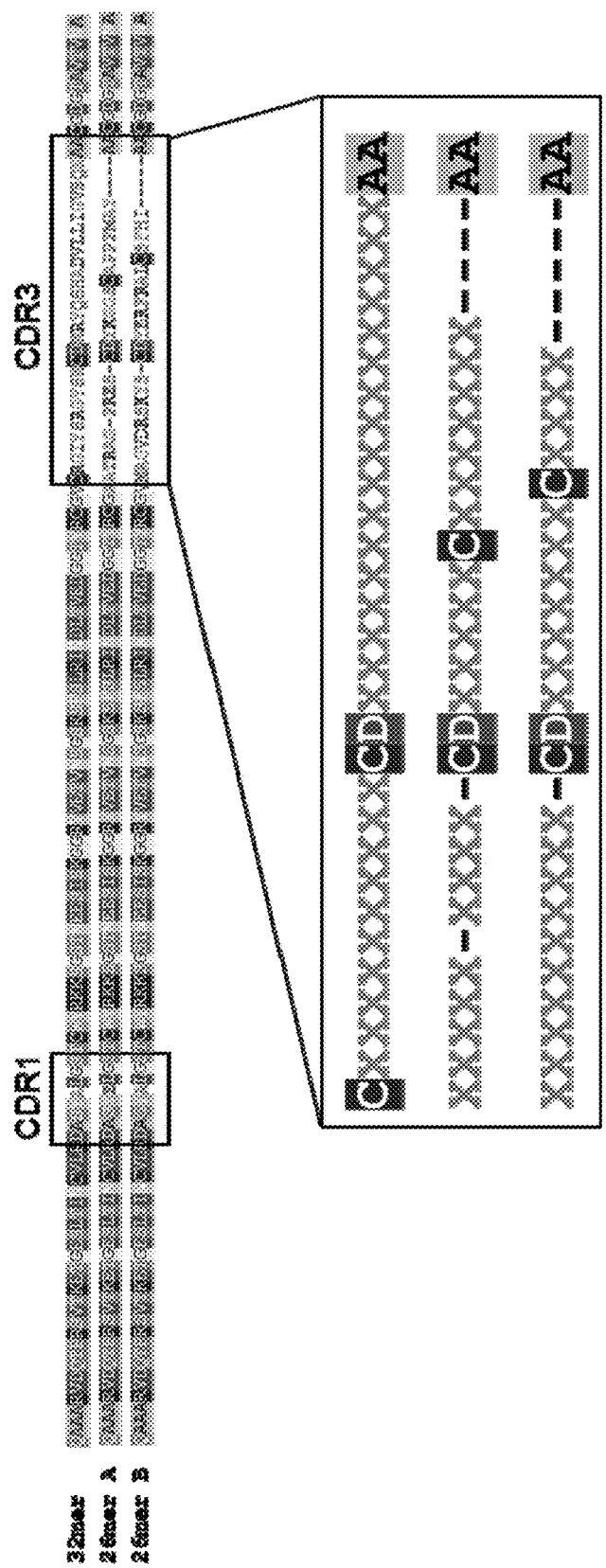
FIG. 4 shows selected templates and the randomization approach. Highlighted residues were conserved.

The VNAR library was generated by overlap PCR (FIG. 2) incorporating all of the above information. A mixture of the ten selected templates was used to introduce framework mutations, while a mixture of oligonucleotides was used to incorporate both randomization of the CDR3 by NNK codons, fixed and loose cysteine residues by use of TGC and DRY codons, and sequence variability on both edges of the CDR (FIGS. 3-4).

The main differences with previously built libraries are that: (i) a nurse shark backbone was used; (ii) selected mutations were introduced in the framework regions; and (iii) amino acids permutations, reflecting naturally occurring variations, were introduced on the edges of the CDR3s.

A Type 1 nurse shark VNAR semi-synthetic library was built from three specific clones identified by randomly sequencing VNARs in naïve libraries built from two different adult nurse sharks. These clones harboured unusually long CDR3 regions of 26 and 32 amino acids and had very few framework mutations (FIG. 4). In order to generate a semi-synthetic library specifically enriched for clones harbouring long CDR3s, the CDR3 of these 3 clones was randomized, as previously described, by overlap PCR, keeping only the two cysteine residues unchanged in order to preserve the structural integrity of the molecule.

The main differences with previously built libraries are that: (i) a nurse shark backbone was used; (ii) a VNAR Type 1 library was used; and (iii) the library is biased for extended CDR3s.

Isolating BAFF Binding VNAR Sequences

Figure 5:
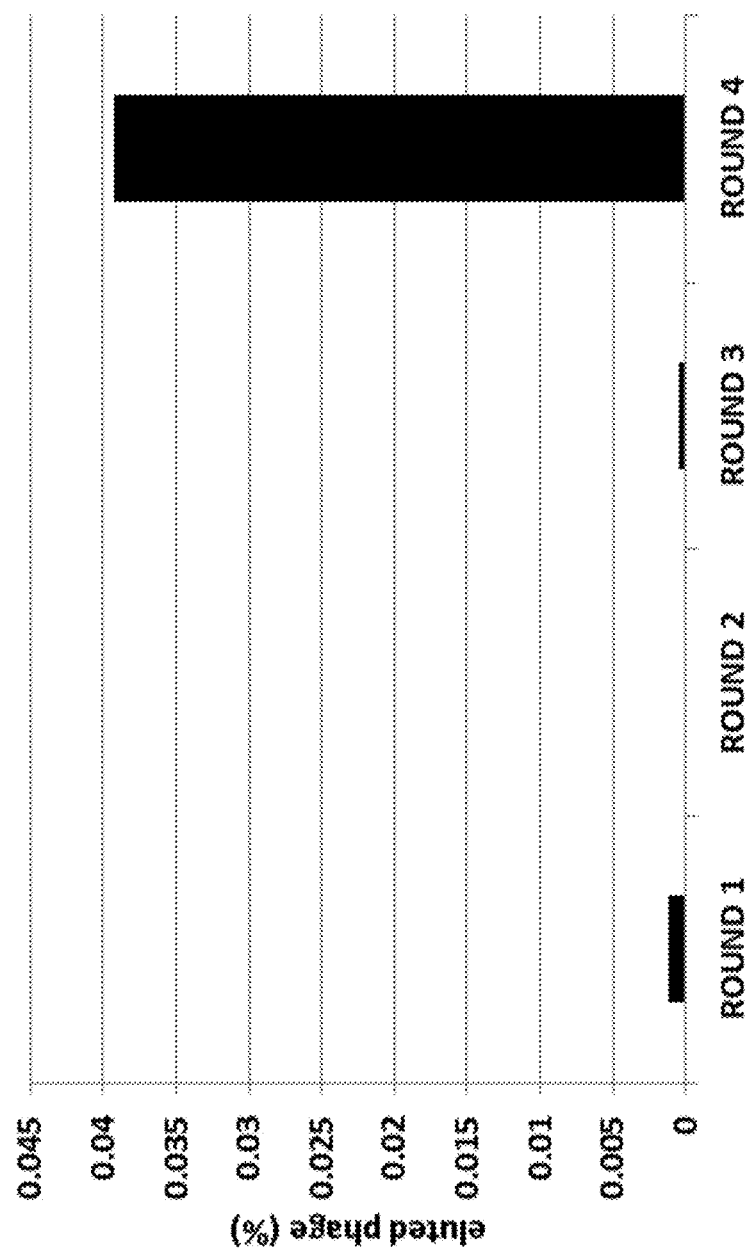
FIG. 5 shows the percentage of eluted phages after each round of selection (see Example 2). The number of phages eluted from the BAFF-coated wells after each round of selection is indicated as a percentage of the amount of phages that were incubated on the plate.

VNARs capable of specifically and selectively binding to human BAFF (hBAFF) were isolated by four rounds of selection and amplification of a semi-synthetic phage display library on immobilized hBAFF recombinant protein (Example 2). In order to select for high affinity clones, the stringency of selection was increased at each round by decreasing hBAFF concentration and increasing the number of washing steps. The efficiency of the selection procedure was assessed by plotting the percentage of eluted phages after each selection round. A 3000-fold increase in phage recovery was observed between rounds 2 and 4 (FIG. 5).

Figure 6:
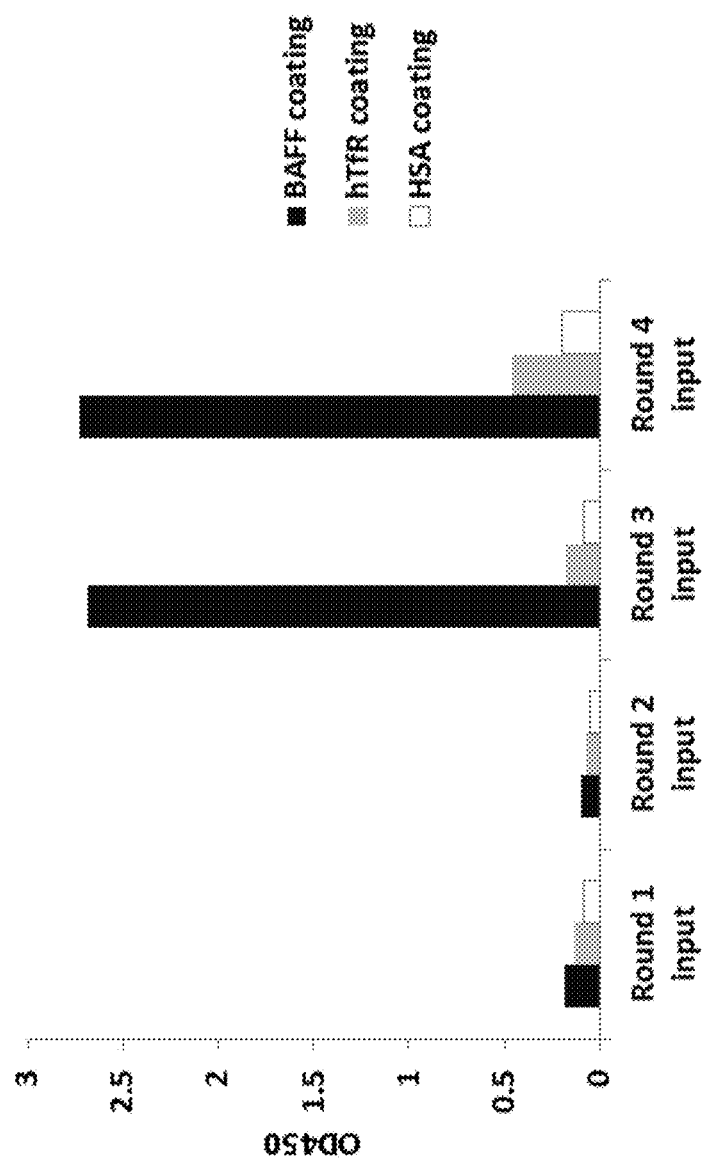
FIG. 6 shows polyclonal phage ELISA on selection outputs from the library constructed according to Example 1. Phages ($1\times10^{12}$) from each round's input were incubated in microwells coated with either human BAFF (hBAFF), or negative VNAR controls (hTfR or HSA). After washing steps, bound phages were detected and quantified using a specific anti-M13 antibody.

The BAFF binding specificity of selected phages was confirmed by a polyclonal phage ELISA in which three different coatings were used (BAFF, hTfR, and HSA). A strong increase in binding phage was observed from round 3, specifically on the BAFF-coated surface and not on other coatings (FIG. 6).

Screening for hBAFF Binding Clones

In order to test the ability of individual clones to bind hBAFF, 93 independent clones were randomly selected in the outputs of both rounds three and four (Example 2). The periplasmic fraction of these clones (containing monomeric VNAR molecules) was exposed to a hBAFF-coated surface (in an ELISA format) and the bound VNARs were detected using a specific antibody. More than 90% of the selected clones appeared hBAFF-specific using this method, with no notable background on a HSA-coated surface.

Figure 7:
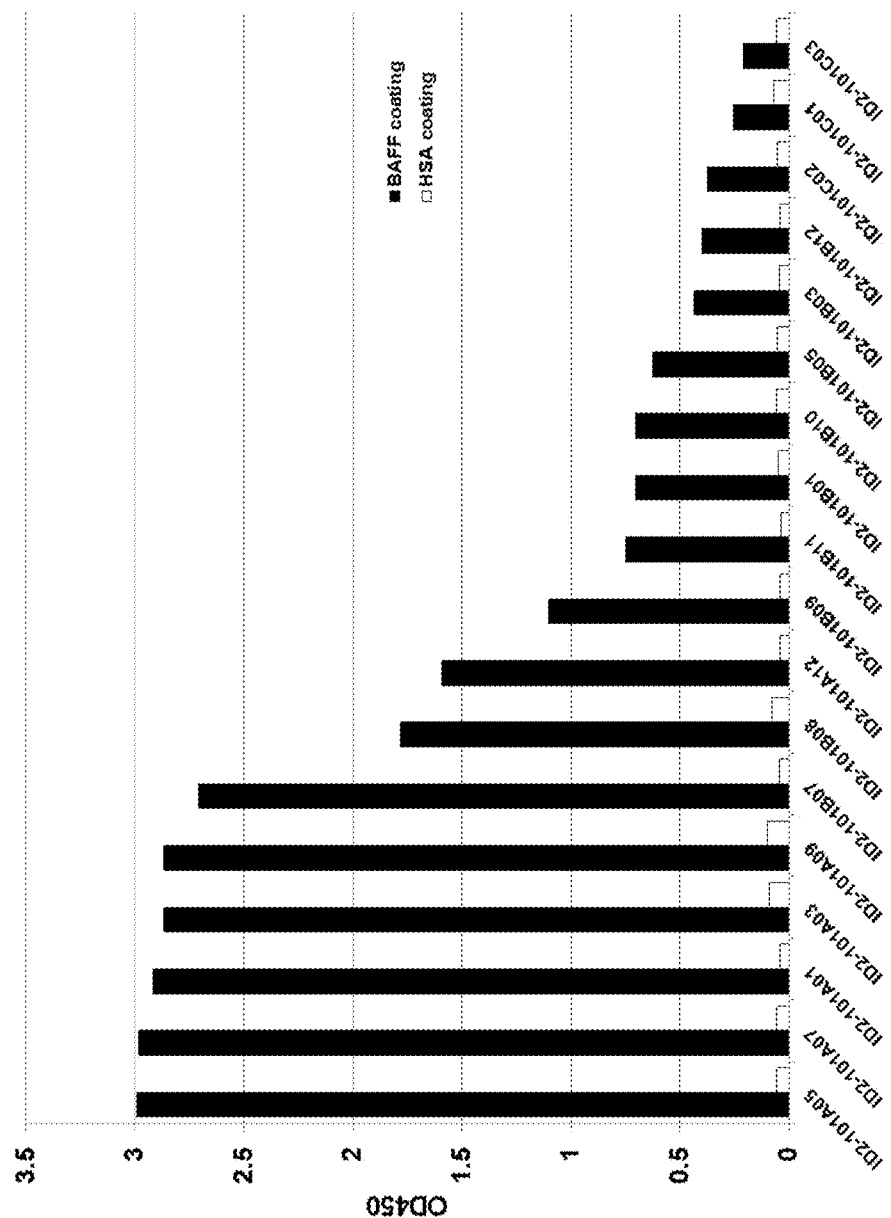
FIG. 7 shows results from screening for hBAFF binding clones. Eighteen unique clones (based on their DNA sequences) were selected for binding specifically to hBAFF in an ELISA format (see Example 2; threshold=four times negative VNAR control, HSA).

The DNA sequence of positive clones was determined and the binding clones were sorted into categories based on their sequence identities. Eighteen unique sequences were selected this way, using a threshold of higher than four for the ratio of BAFF-binding signal to HSA-binding signal (FIG. 7). Interestingly, the vast majority of binding clones appear to harbour a DXL motif in their CDR3, just upstream of the single cysteine (see Table I, below). This motif was previously described as being part of the main binding site of BAFF to its receptor.

TABLE 1

Protein sequence of isolated BAFF binding VNARs (DXL motifs are highlighted in bold, CDR3 cysteine(s) are underlined)

| Clone ID2- | SEQ ID NO: | FW1 | CDR1 |
|---|---|---|---|
| 101A05 | 4 | AQAAARVDQTPQTITKETGESLTINCVLR | DNNCALS |
| 101A07 | 5 | AQAAARVDQTPQTITKETGESLTINCVLR | DSNCALS |
| 101A01 | 6 | AQAAARVDQTPQTITKETGESLTINCVLR | DSNCALS |
| 101A03 | 7 | AQAAARVDQTPQTITKETGESLTINCVLR | DNNCALS |
| 101A09 | 8 | AQAAARVDQTPQTITKETGESLTINCVLR | DNNCALS |

TABLE 1-continued

Protein sequence of isolated BAFF binding VNARs (DXL motifs are highlighted in bold, CDR3 cysteine(s) are underlined)

| Clone ID2- | SEQ ID NO: | FW1 | CDR1 |
|---|---|---|---|
| 101B07 | 9 | AQAAARVDQTPRSVTKETGESLTINCVLR | DSICALS |
| 101B08 | 10 | AQAAARVDQTPQTITKETGESLTINCVLR | DSNCALS |
| 101A12 | 11 | AQAAARVDQTPQTVTKETGESLTINCVLR | DASYALG |
| 101B09 | 12 | AQAAARVDQTPQTITKETGESLTINCVLR | DSNCALP |
| 101611 | 13 | AQAAARVDQTPRSVTKETGESLTINCVLR | DSNCALS |
| 101601 | 14 | AQAAARVDQTPQTITKETGESLTINCVLR | DSNCALS |
| 101610 | 15 | AQAAARVDQTPQTITKETGESLTINCVLR | DSNCALS |
| 101B05 | 16 | AQAAARVDQTPRSVTKETGESLTINCVLR | DSICALS |
| 101B03 | 17 | AQAAARVDQTPRSVTKETGESLTINCVLR | DNNCALS |
| 101B12 | 18 | AQAAARVDQTPQTITKETGESLTINCVLR | DSNCALS |
| 101C02 | 19 | AQAAARVDQTPQTITKETGESLTINCVLR | DNNCALS |
| 101C01 | 20 | AQAAARVDQTPQTITKETGESLTINCVLR | DNNCALS |
| 101C03 | 21 | AQAAARVDQTPRSVTKETGESLTINCVLR | DSICALS |

| Clone ID2- | FW2-3 | CDR3 | FW4 |
|---|---|---|---|
| 101A05 | TTYWYRKKSGSTNEENISKGGRYVETVNSGSKSFSLRINDLTVEDSGTYRCKV | SKDWLLCRDRGRRETDV | YGDGTAVTVNAASGAHHHHHHGADYKDDDDK* |
| 101A07 | NLYWYRKKSGSTNEESISLGGRYVETVNSGSKSFSLRINDLTVEDSGTYRCKV | QLPYDPLTKECILGRMDV | YGDGTAVTVNAASGAHHHHHHGADYKDDDDK* |
| 101A01 | NLYWYRKKSGSTNEESISLGGRYVETVNSGSKSFSLRINDLTVEDSGTYRCKV | RRARVIGGEYCRVQWQDV | YGGGTAVTVNAASGAHHHHHHGADYKDDDDK* |
| 101A03 | TTYWYRKKSGSTNEENISKGGRYVETVNSGSKSFSLKINDLTVEDSGTYRCKV | RVDRLLCGWRVGRRQLGDV | YGGGTVVTVNAASGAHHHHHHGADYKDDDDK* |
| 101A09 | TTYWYRKKSGSTNEESISKGGRYVETVNSGSKSFSLRINDLTVEDSGTYRCKV | REDPLMCRYYLDRYRDV | YGGGTVVTVNAASGAHHHHHHGADYKDDDDK* |
| 101B07 | STHWYRKKSGSTNEESISKGGRYVETVNSGSKSFSLRINDLTVEDSGTYRCKV | HGGRSTGLCGDVLLAGDV | YGGGTAVTVNAASGAHHHHHHGADYKDDDDK* |
| 101B08 | STLWYRTKSGSRNEESISKGGRYVETVNSGSKSFSLKINDLTVEDSGTYRCKV | PRDLLLCKRPRARLPDV | YGGGTAVTVNAASGAHHHHHHGADYKDDDDK* |
| 101A12 | STCWYRKKSGSRNEESISKGGRYVETVNSGSKSFSLRINDLTVEDSGTYRCKV | RDPLLFPRDRCDGESKDV | YGGGTVVTVNAASGAHHHHHHGADYKDDDDK* |
| 101B09 | STYWYRKKSGSTNEESISLGGRYVETVNSGSKSFSLRINDLTVEDSGTYRCKV | LSNVHICCRFGSCADV | YGDGTAVTVNAASGAHHHHHHGADYKDDDDX* |
| 101611 | STYWYRKKSGSTNEENISKGGRYVETVNSGSKSFSLRINDLTVEDSGTYRCKV | MLDPLLCPALLESMTDV | YGGGTAVTVNAASGAHHHHHHGADYKDDDDK* |
| 101601 | STYWYRKKSGSTNEESISKGGRYVETVNSGSKSFSLRINDLTVEDSGTYRCNV | APTIISGCSIKRRDV | YGGGTAVTVNAASGAHHHHHHGADYKDDDDK* |
| 101610 | STYWYRKKSGSTNEESISKGGRYVETVNSGSKSFSLRINDLTVEDSGTYRCKV | RIDPLLCNASYVKWDDV | YGGGTVVTVNAASGAHHHHHHGADYKDDDDK* |
| 101B05 | STHWYRKKSGSTNEESISKGGRYVETVNSGSKSFSLRINDLTVEDSGTYRCKV | NHDLLTSSRRCQSQIKDV | YGGGTVVTVNAASGAHHHHHHGADYKDDDDK* |
| 101B03 | TTYWYRKKSGSTNEENISKGGRYVETVNSGSKSFSLRINDLTVEDSGTYRCKV | KPDLLFCSSSGLGLIQDV | YGGGTAVTVNAASGAHHHHHHGADYKDDDDK* |
| 101B12 | STYWYRKKSGSTNEESISKGGRYVETVNSGSKSFSLRINDLTVEDSGTYRCKV | FIDPLLCSRDALGFSDV | YGDGTAVTVNAASGAHHHHHHGADYKDDDDK* |

TABLE 1-continued

Protein sequence of isolated BAFF binding VNARs (DXL motifs are highlighted in bold, CDR3 cysteine(s) are underlined)

| Clone ID2- | SEQ ID NO: | FW1 | CDR1 | |
|---|---|---|---|---|
| 101C02 | | TTYWYRKKSGSTNEENISKGGRYVET VNSGSKSFSLKINDLTVKDSGTYRCKV | TRDPLF<u>C</u>SYRASKRHDV | YGGGTVVTVNAASGAH HHHHHGADYKDDDDK* |
| 101C01 | | TTYWYRKKSGSTNEENISKGGRYVET VNSGSKSFSLRINDLTVEDSGTYRCKV | RLDLLL<u>C</u>RNGSTNSIDV | YGGGTAVTVNAASGAH HHHHHGADYKDDDDK* |
| 101C03 | | STHWYRKKSGSTNEESISLGGRYVETV NSGSKSFSLKINDLTVEDSGTYRCKV | TRYVVFSGST<u>C</u>RMRRADV | YGGGTVVTMNAASGAH HHHHHGADYKDDDDK* |

Screening for hBAFF/BAFF-R Blocking Clones

Figure 8:
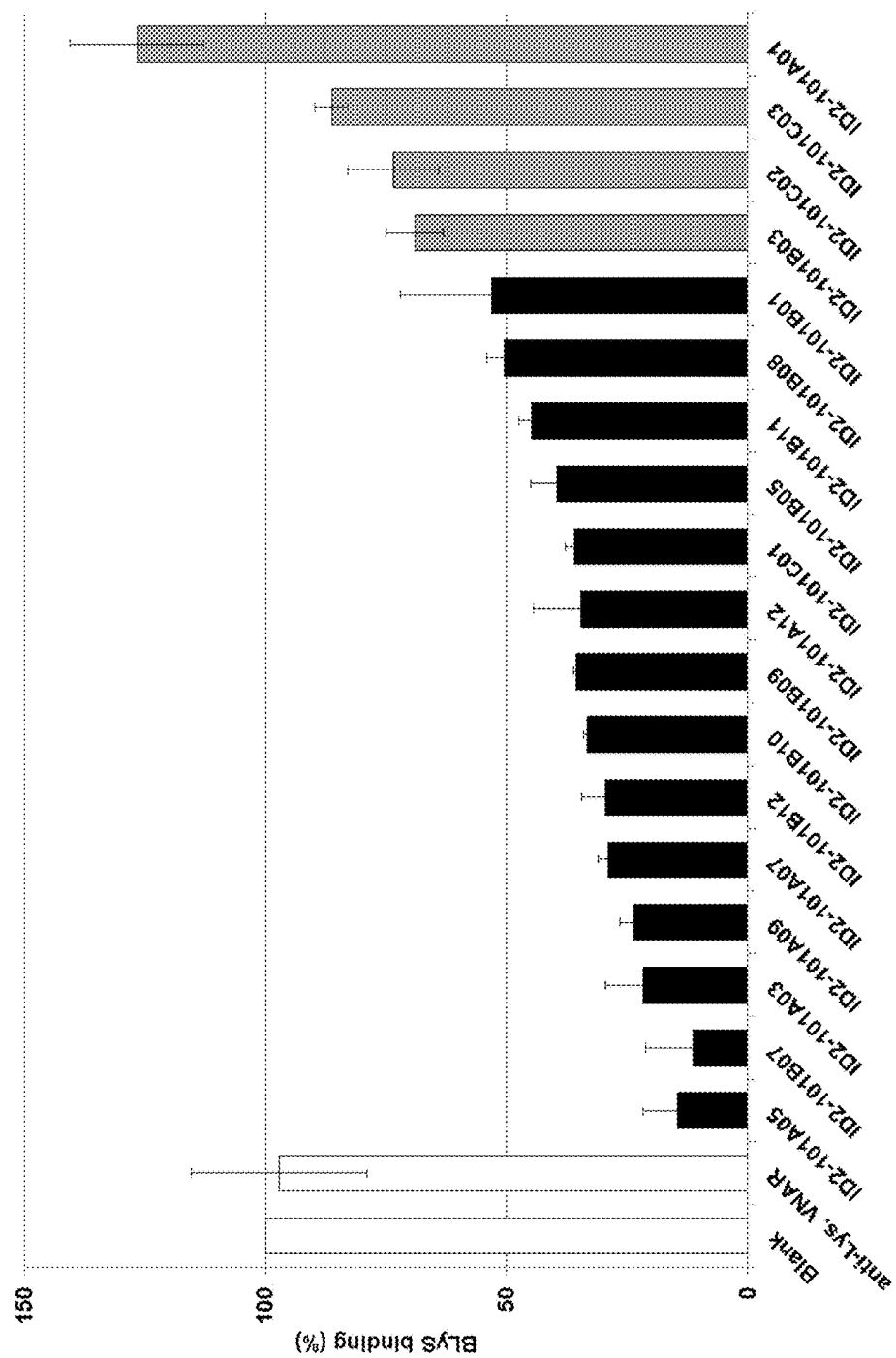
FIG. 8 shows results from screening for hBAFF blocking clones. Fourteen of the eighteen binding clones are capable of inhibiting BAFF/BAFF-R (BLys) binding by at least 50% in a blocking ELISA format. Negative controls are shown in white. Clones that inhibit BAFF/BAFF-R binding by less than 50% are shown in grey (see Example 2).

In order to test the ability of the eighteen selected BAFF binding clones to block the interaction between BAFF and its receptor, BAFF-R, a periplasmic fraction from each clone was pre-incubated with recombinant hBAFF before being exposed to a surface coated with BAFF-R. Ability to block the BAFF/BAFF-R interaction was then measured by specifically detecting the amount of BAFF bound to the plate by using a specific antibody, as described in Example 2. As used herein, a blocking clone is one that is capable of inhibiting binding of BAFF to its receptor by at least 50%. Using these criteria, fourteen of the eighteen binding clones appeared to prevent the BAFF/BAFF-R interaction (FIG. 8; Example 2).

$EC_{50}$ values may be used as a numerical measure of potency, such as for ability to bind with a given binding partner, e.g., a ligand or receptor. An $EC_{50}$ value is a measure of the concentration of a compound required to achieve half of that compound's maximal activity in a particular assay (Example 3). An $IC_{50}$ value or inhibition constant is the concentration which inhibits binding of one agent to another agent by 50% and may also be used as a numerical measure of the ability of a BAFF binding moiety or antagonist compound to compete with a different BAFF binding agent, e.g., an anti-BAFF antibody, for binding to BAFF, e.g., to human BAFF (Example 3).

Binding affinities may be measured as a constant of binding affinity ($K_A$), or as a constant of dissociation from a bound complex ($K_D$). In some embodiments, compounds of the present invention, the $K_A$ or $K_D$ towards hBAFF is below 20 nM. In some embodiments of compounds of the present invention, the $K_A$ or $K_D$ towards hBAFF is below 10 nM. In further embodiments of compounds of the present invention, the $K_A$ or $K_D$ towards hBAFF is below 5 nM. In still further embodiments of compounds of the present invention, the $K_A$ or $K_D$ towards hBAFF is below 1 nM.

Biological Activities of Selected VNARs

In order to test the ability of selected VNARs to inhibit BAFF biological activity, each of the lead molecules was tested in a mouse splenocyte survival assay where mouse splenic B cells were exposed to BAFF in the presence or in the absence of a putative BAFF antagonist VNAR. Six of the lead VNARs did not appear to affect BAFF bioactivity. An IC50 was determined for five of the remaining seven lead VNARs, ranging from 60 to 200 nM, which is in the same order of magnitude as hBAFF-R, known to display an IC50 of 120 nM.

A summary of biochemical data of selected BAFF selective VNAR clones is shown in Table 2. These data include EC50 and IC50 measurements as well as an indication in certain cases as to whether a BAFF antagonist compound, selected for its ability to bind to hBAFF, exhibits cross reactivity in the mouse, i.e., binds to both human and mouse BAFF. Such cross-reactive BAFF binding moieties and compounds will be useful in conducting experiments in animals, e.g., mouse B cell related disease models. The following are representative for binding or inhibition of binding by a BAFF specific VNAR monomer according to the invention. Therapeutic versions, including variants and derivatives thereof, are expected to be more potent.

TABLE 2

Biochemical data summary of selected clones

| CLONE NAME | ELISA EC50 (nM) | ELISA IC50 (nM) | Inhibition of BAFF Bioactivity | CELLULAR IC50 (nM) | Mouse cross-reactivity |
|---|---|---|---|---|---|
| ID2-101A07 | 0.5 | 6.8 | ++ | 58 | ++++ |
| ID2-101B07 | 0.8 | 6.8 | ++ | 60 | ---- |
| ID2-101A05 | 1.5 | 13.8 | ++ | 135 | ++ |
| ID2-101B10 | 1 | 2.8 | ++ | ≈100 | + |
| ID2-101A09 | 4.9 | 9.7 | ++ | 215 | ++ |
| ID2-101C01 | 2.13 | 3.85 | ++ | n.d. | n.d. |
| ID2-101A12 | 4.57 | 49.16 | ++ | n.d. | n.d. |
| ID2-101B11 | 2.49 | 6.85 | – | n.d. | n.d. |
| ID2-101B12 | 2.7 | 9.32 | – | n.d. | n.d. |
| ID1-101B09 | 4.07 | 36.77 | – | n.d. | n.d. |
| ID2-101B01 | 7.4 | 91.2 | – | n.d. | n.d. |
| ID2-101A03 | 17.16 | 12.33 | – | n.d. | n.d. |
| ID2-101B05 | 11.82 | 148.2 | – | n.d. | n.d. |

Polypeptide Sequences and Compounds Comprising a BAFF Specific VNAR

The present invention provides a BAFF specific binding moiety, e.g., polypeptide, and BAFF antagonist compounds comprising BAFF specific binding moieties. Isolated BAFF binding VNARs are also provided. In certain embodiments, the BAFF specific binding moiety is specific for a mammalian BAFF. In certain embodiments, the BAFF binding moiety is specific for human BAFF. In certain embodiments, the BAFF specific binding moiety comprises a DXL motif in its CDR3 region. In certain embodiments, the BAFF specific binding moiety blocks the interaction between hBAFF and its receptor, BAFF-R.

In certain embodiments, the BAFF specific binding moiety comprises a CDR 1 region and a CDR3 region interspersed by a framework region (see FW2-3 in Table 1 and below), in which the CDR 1 region comprises or consists essentially of a peptide having an amino acid sequence of formula: D-$X_2$-$X_3$-$X_4$-A-L-$X_7$ (SEQ ID NO: 1)

wherein X$_2$ is N or S;
X$_3$ is N, I or S;
X$_4$ is C or Y; and
X$_7$ is S, P or G.

In certain aspects of this embodiment, the CDR 1 region, which in naturally-occurring VNARs is a conserved seven amino acid residue stretch, comprises or consists essentially of a peptide selected from DNNCALS (SEQ ID NO: 22), DSNCALS (SEQ ID NO: 23), DSNCALP (SEQ ID NO: 24), DSICALS (SEQ ID NO: 25) or DASYALG (SEQ ID NO: 26) (Table 1).

The CDR3 region in naturally-occurring VNARs is of heterogeneous size, ranging from about 7 to about 32 amino acid residues in length. In synthetic VNAR libraries exemplifying the present invention, CDR3 regions of 11 to 18 residues, and 26 or 32 residues, were constructed.

In certain other embodiments of the invention, the BAFF specific binding moiety comprises a CDR 1 region and a CDR3 region interspersed by a framework region (see FW2-3 in Table 1 and below), wherein the CDR 3 region comprises a peptide having an amino acid sequence of formula (a) D-X$_a$-L-Z$_{(1-6)}$—C (SEQ ID NO: 2);
wherein X$_a$ is selected from W, P, R, V or L; and Z$_{(1-6)}$ is a stretch of any one to six amino acid residues.

In certain other embodiments of the invention, the BAFF specific binding moiety comprises a CDR 1 region and a CDR3 region interspersed by a framework region (see FW2-3 in Table 1 and below), wherein the CDR 3 region comprises a peptide having an amino acid sequence of formula (b) C—Z$_{(1-6)}$-D-X$_a$-L (SEQ ID NO: 3);
wherein X$_a$ is selected from W, P, R, V or L; and Z$_{(1-6)}$ is a stretch of any one to six amino acid residues. In certain embodiments of peptides having an amino acid sequence of either formula (a) or (b), Z$_{(1-6)}$ is one amino acid residue selected from G, L, F or M.

In certain aspects of the above embodiments of the invention, the BAFF specific binding moiety comprises a CDR3 region which comprises a peptide selected from DWLLC (SEQ ID NO: 27), DPLLC (SEQ ID NO: 28), DRLLC (SEQ ID NO: 29), DLLLC (SEQ ID NO: 30), DLLFC (SEQ ID NO: 31), DPLFC (SEQ ID NO: 32), DPLMC (SEQ ID NO: 33), DPLTKEC (SEQ ID NO: 34), DLLTSSRRC (SEQ ID NO: 35), DPLLFPRDRC (SEQ ID NO: 36) or HGGRSTGLCGDVLLAGDV (SEQ ID NO: 37).

In certain other aspects of the above embodiments of the invention, the BAFF specific binding moiety comprises a CDR 3 region which comprises a peptide selected from RRARVIGGEYCRVQWQDV (SEQ ID NO: 38), LSNVHICCRFGSCADV (SEQ ID NO: 39), APTIISGCSIKRRDV (SEQ ID NO: 40), or TRYVVFSGSTCRMRRADV (SEQ ID NO: 41).

The present invention further provides a BAFF specific binding moiety comprising a CDR1 region comprising any one of the CDR1 peptide sequences shown in Table 1 in combination with a CDR3 region comprising any one of the CDR3 peptides shown in Table 1, separated by a framework region (see FW2-3 in Table 1), each as an independent embodiment of the invention. In certain embodiments, the framework region interspersed between CDR1 and CDR3 comprises any one of the FW2-3 amino acid sequences shown in Table 1. The FW2-3 region in naturally-occurring VNARs is 53 amino acids in length, with insertions and deletions rarely observed. The FW2-3 region comprises hypervariable regions HV2 and HV4 (see FIG. 1; and B. J. Fennell et al., *J Mol Biol.* 400 (2010) pp. 155-170) which display some sequence variability and hence which can be suitable regions in which amino acid residues may be modified to create a variant of the BAFF specific binding moiety of the invention.

In any one of the individual embodiments described above, the BAFF specific binding moiety may further comprise one or more of the FW1, FW2-3 or FW4 amino acid sequences shown in Table 1, in any functional combination. The present invention further provides a BAFF specific binding moiety comprising one of the eighteen cloned peptide sequences shown in Table 1.

Therefore, in one aspect, the invention provides a BAFF antagonist compound comprising or consisting essentially of a VNAR derived BAFF specific binding moiety which binds selectively to a BAFF polypeptide, preferably to human BAFF (Q9Y275-1) or to an epitope-containing fragment of BAFF.

In one embodiment, a BAFF specific binding moiety or BAFF antagonist compound of the invention binds to the target protein BAFF and decreases or inhibits BAFF binding to BAFF-R. In other embodiments, the BAFF specific binding moiety or BAFF antagonist compound inhibits BAFF induced human B cell proliferation, and/or immunoglobulin production. In certain embodiments, a BAFF specific binding moiety or BAFF antagonist compound of the invention depletes B cells in vitro. In other certain embodiments, a BAFF specific binding moiety or BAFF antagonist compound of the invention depletes B cells in vivo.

BAFF antagonist compound activity ("BAFF bioactivity") may be determined by one or more assays used to measure an activity which is either antagonism or agonism by an antibody. In certain embodiments, binding of the BAFF antagonist compound to BAFF is measured by a well-known immunoassay, such as for example an ELISA as described in Examples 2 and 3. Any other binding assay which measures direct or indirect interaction of the BAFF antagonist compound to BAFF, or alternatively, which measure the ability of a BAFFantagonist compound of the invention to compete for binding to BAFF in the presence of a different BAFF binding compound (such as an anti-BAFF antibody) such as by a competitive inhibition assay, may be used. Preferably, a selected assay measures the effect of a BAFF antagonist compound of the invention on at least one biological effect of native BAFF and in certain embodiments, compares the effect to that of another native BAFF binding agent, e.g., to an anti-BAFF antibody. In vivo assays of BAFF bioactivity include, but are not limited to: a mouse splenocyte assay such as that described in Example 5; BAFF induced human B cell proliferation, IgGI production and/or human B cell depleting activity.

Results of cellular in vitro assays may be further verified using one or more in vivo animal models. A variety of accepted animal models of immune-related diseases or cancers may be used to characterize, e.g., test the efficacy of, a BAFF antagonist compound or composition of the invention. Animal models of immune-related diseases include both non-recombinant and recombinant (transgenic) animals. Tissue specific autoimmune diseases such as multiple sclerosis (MS) and experimental autoimmune encephalomyelitis (EAE, a model for MS) in animal models may be useful in characterizing BAFF antagonist compounds of the invention (see, e.g., Current Protocols in Immunology, unit 4.5). An accepted animal model for human autoimmune rheumatoid arthritis is collagen-induced arthritis. Mouse and rat models are characterized by synovitis, and erosion of cartilage and subchondral bone. BAFF antagonist compounds of the invention may be tested for activity against autoimmune arthritis using such protocols (see, e.g., Current Protocols in Immunology, unit 15.5; see also Issekutz, A. C. et al., *Immunology*, (1996) 88:569).

In one embodiment, the invention provides BAFF specific binding moieties which bind to a region of BAFF that interacts with BAFF-R. In a related embodiment, the invention provides BAFF specific binding moieties which bind to a region of BAFF between amino acids 200 and 275 of UniProtKB/Swiss-Prot: Q9Y275-1 (see also FIG. 4 of Gordon N C et al., *Biochemistry*. 2003 May 27; 42(20):5977-83 for the BAFF/BLyS Receptor 3 minimal TNF receptor-like module that encodes a highly focused ligand-binding site.)

According to another embodiment, a BAFF antagonist compound of the invention binds to human BAFF in a standard ELISA or other similar assay with an EC50 of 300 nM or less, and preferably 100 nM or less, 10 nM or less, or 1 nM or less. Thus, a BAFF antagonist compound of the invention binds to BAFF, e.g., hBAFF, in a standard ELISA or other similar assay with an EC50 in a range of 0.1 nM to 300 nM, 0.5 nM to 300 nM, 1 nM to 300 nM, 10 nM to 300 nM, 50 nM to 300 nM, 100 nM to 300 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, 5 nM to 50 nM, 10 nM to 50 nM.

According to another embodiment, a BAFF antagonist compound of the invention competes with another antibody specific for binding to human BAFF in a standard ELISA or other similar assay with an IC50 of 1 micromolar or less, 500 nM or less, and preferably 100 nM or less, 50 nM or less, 25 nM or less, 10 nM or less, or 1 nM or less. Thus, a BAFF antagonist compound of the invention competes for binding to BAFF, e.g., hBAFF, in a standard ELISA or other similar assay with an IC50 in a range of 0.1 nM to 1 micromolar, 1 nM to 1 micromolar, 10 nM to 1 micromolar, 100 nM to 1 micromolar, 0.1 nM to 500 nM, 0.5 nM to 500 nM, 1 nM to 500 nM, 10 nM to 500 nM, 50 nM to 500 nM, 100 nM to 500 nM, 250 nM to 500 nM, 0.1 nM to 250 nM, 0.5 nM to 250 nM, 1 nM to 250 nM, 5 nM to 250 nM, 10 nM to 250 nM, 50 nM to 250 nM, 100 nM to 250 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, or 10 nM to 50 nM.

According to another embodiment, a BAFF antagonist compound of the invention depletes B cells in vitro with an $EC_{50}$ of 500 nM or less, 300 nM or less, preferably 250 nM or less, 100 nM or less, 50 nM or less, 10 nM or less, 1 nM or less or 100 pM or less. Thus, a BAFF antagonist compound of the depletes B cells in vitro with an $EC_{50}$ in a range of 0.1 nM to 500 nM, 0.5 nM to 500 nM, 1 nM to 500 nM, 10 nM to 500 nM, 50 nM to 500 nM, 100 nM to 500 nM, 250 nM to 500 nM, 0.1 nM to 250 nM, 0.5 nM to 250 nM, 1 nM to 250 nM, 5 nM to 250 nM, 10 nM to 250 nM, 50 nM to 250 nM, 100 nM to 250 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, or 10 nM to 50 nM.

According to another embodiment, a BAFF antagonist compound of the invention inhibits B cell proliferation in a splenocyte proliferation assay or other similar in vitro cellular assay with an IC50 of 500 nM or less, 300 nM or less, preferably 250 nM or less, 100 nM or less, 50 nM or less, 10 nM or less, or 1 nM or less. Thus, a BAFF antagonist compound of the inhibits B cell proliferation in a splenocyte proliferation assay or other similar in vitro cellular assay with an IC50 in a range of 0.1 nM to 500 nM, 0.5 nM to 500 nM, 1 nM to 500 nM, 10 nM to 500 nM, 50 nM to 500 nM, 100 nM to 500 nM, 250 nM to 500 nM, 0.1 nM to 250 nM, 0.5 nM to 250 nM, 1 nM to 250 nM, 5 nM to 250 nM, 10 nM to 250 nM, 50 nM to 250 nM, 100 nM to 250 nM, 0.1 nM to 100 nM, 0.5 nM to 100 nM, 1 nM to 100 nM, 5 nM to 100 nM, 10 nM to 100 nM, 0.1 nM to 50 nM, 0.5 nM to 50 nM, 1 nM to 50 nM, or 10 nM to 50 nM.

The binding affinity, EC50 and IC50 ranges recited above are for measurements on a BAFF specific VNAR monomer according to the present invention. Therapeutic versions of the invention include other molecular configurations, e.g., VNAR monomers fused to stabilizing heterologous peptide regions, e.g., the Fc domain of an IgG or other immunoglobulin molecule, which may be expressed and then further purified as multimers, such as covalent dimers. We envision that the activity of certain such therapeutic molecules will have even greater potency, preferably by at least 2-10 fold higher potencies.

BAFF bioactivity may also or alternatively be measured by BAFF binding affinity, using any of a number of assays known in the art, such as a surface plasmon resonance assay (Example 5). According to another embodiment, a BAFF antagonist compound of the invention binds to human BAFF in an affinity assay such as by surface plasmon resonance assay with a binding affinity of 300 nM or less, and preferably 100 nM or less, 10 nM or less, 1 nM or less or 100 pM or less. Thus, a BAFF antagonist compound of the invention binds to BAFF, e.g., hBAFF, with an affinity constant ($K_A$) in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to BAFF, e.g., hBAFF, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 10 nM, as measured, e.g., by surface plasmon resonance such as in a BIACore assay.

In another related embodiment, treatment of an accepted mouse model with a BAFF antagonist of the invention can reduce the percentage of B cells in the blood or a tissue in vivo up to 70%, preferably up to 75%, more preferably up to 80%, 90% or higher as compared to untreated control animals.

In some embodiments, BAFF antagonist compounds of the invention are specific to human BAFF and do not measurably cross-react with other cross reactive ligands, such as with APRIL. In some embodiments, BAFF antagonist compounds of the invention are selective for binding to human BAFF relative to cross reactive ligands, such as APRIL. In certain embodiments, the BAFF compound of the invention binds to hBAFF with a 5-fold, 10-fold, 20-fold, 50-fold, 100-fold, 500-fold or more higher affinity compared to its binding affinity to a cross reactive ligand, such as APRIL. In some embodiments, a BAFF antagonist compound of the invention is specific to human BAFF but also binds to or cross-reacts with one or more other mammalian BAFFs, e.g., with mouse BAFF (UniProtKB/Swiss-Prot: Q9WU72).

Pharmaceutically acceptable salts or solvates of any of the BAFF specific binding compounds of the invention are likewise within the scope of the present invention.

As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., BAFF binding moieties, BAFF antagonist peptides and compounds), and pharmaceutically acceptable salts and solvates thereof, constitutes an individual embodiment of the invention.

Derivatives, Variants, Conjugates

The invention further provides variants of a BAFF specific binding moiety of the invention, wherein the variant differs from the recited amino acid sequence by up to 1, 2, 3, 4, 5, 6, 7, 8, 9, 10 or more amino acid residues (but by no more than that which retains 85%, 90%, 95%, 99% or more amino acid sequence identity) and retains BAFF bioactivity. BAFF bioactivity is measured by BAFF binding affinity, using any of a number of assays know in the art. In certain embodiments, a compound of the invention binds to BAFF, e.g., hBAFF, with an affinity constant in a range of 0.1 nM to 500 nM, 0.5 nM to 500 nM, or 1 nM to 500 nM, 0.1 nM to 250 nM, 0.5 nM to 250 nM, or 1 nM to 250 nM as measured, e.g., by surface plasmon resonance such as in a BIACore assay. In certain embodiments, a compound of the invention binds to BAFF, e.g., hBAFF, with an affinity constant in a range of 0.1 nM to 100 nM, 0.1 nM to 50 nM, or 0.1 nM to 10 nM, 0.5 nM to 100 nM, 0.5 nM to 50 nM, or 0.5 nM to 10 nM, or 1 nM to 100 nM, 1 nM to 50 nM or 1 nM to 10 nM, as measured, e.g., by surface plasmon resonance such as in a BIACore assay. It will be understood by one of skill in the art that amino acid residues outside of the conserved FW, CDR1 and CDR3 motifs are in general regions in which amino acid modifications may be tolerated more readily without deleteriously depleting BAFF binding activity.

A biologically active fragment of any of the foregoing sequences which retains BAFF bioactivity is also encompassed by the present invention. Thus, in further aspects, the invention further comprises compounds having an amino acid sequence that is truncated (shortened), from the N- or C-terminus, relative to the full length sequence of compounds of the invention. In some embodiments, the truncated compounds are truncated by up to 1, 2, 3, 4, 5, 6, 7, 8, 9, 10, 11, 12, 13, 14, 15, 16, 17, 18, 19, 20, 21, 22, 23, 24, 25 or more amino acid residues, counting from the C-terminus of a compound of the invention as disclosed above. Amino acid residue outside of the conserved VNAR framework motifs are regions in which amino acid modifications may be better tolerated without deleteriously depleting BAFF binding activity.

In some embodiments, the compounds of the invention may have at least 40%, e.g., at least 45%, 50%, 55%, 60%, 65%, 70%, 75%, 80%, 85%, 90%, 95%, 96%, 97%, 98%, or 99%, 99.5%, or 99.9% amino acid sequence identity to one of the BAFF antagonists disclosed herein, as long as the compound retains a BAFF biological activity (as measured by BAFF binding affinity, EC50 or IC50) within a range described herein.

Thus in certain, BAFF specific binding compounds of the invention may comprise the amino acid sequence of any one of the compounds shown in Table 1 (see below), or a functional variant thereof that has at least about 70%, 75%, 80%, 85%, 90%, 95%, 97%, 98%, 99% or 99.5% sequence identity to any one of the compounds in Table 1. A functional variant of a polypeptide of the invention may inhibit at least one BAFF bioactivity by any one of the assays disclosed herein by at least 50%, 55%, 60%, 65%, 70%, 75%, 80%, 85%, 90%, 95%, 97%, 98%, 99%, 99.5%, or 100%. In some embodiments, a BAFF antagonist compound of the invention may comprise one or more amino acid substitutions, e.g., conservative amino acid substitutions, and retain BAFF binding activity of at least 50%, 55%, 60%, 65%, 70%, 75%, 80%, 85%, 90%, 95%, 97%, 98%, 99%, 99.5%, or 100% compared to the binding by an unmodified BAFF antagonist compound of the invention, and/or compared to binding of any other available anti-BAFF antibody, such as anti-human BAFF monoclonal antibody belimumab.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). Unless otherwise indicated, reference is made to the L-isomeric forms of the amino acids in question. Where appropriate, the D-isomeric form of an amino acid is indicated in the conventional manner by the prefix "D" before the conventional three-letter code (e.g. DAsp, DPhe).

In certain embodiments, the invention further provides a BAFF specific binding moiety or BAFF antagonist comprising said binding moiety, in which there are one or more conservative amino acid substitutions introduced into the polypeptide sequence. As used herein, the term "conservative substitution" denotes that one or more amino acids are replaced by another, biologically similar amino acid residue. Examples include substitution of amino acid residues with similar characteristics, e. g. small amino acids, acidic amino acids, polar amino acids, basic amino acids, hydrophobic amino acids and aromatic amino acids. See, for example, the table below. An example of a conservative substitution with a residue normally not found in endogenous, mammalian peptides and proteins is the conservative substitution of Arg or Lys with, for example, ornithine, canavanine, aminoethylcysteine or another basic amino acid. For further information concerning phenotypically silent substitutions in peptides and proteins, see, e.g., Bowie et al., *Science* 247, 1306-1310, 1990. In the scheme below are conservative substitutions of amino acids grouped by physicochemical properties. I: neutral, hydrophilic, II: acids and amides, III: basic, IV: hydrophobic, V: aromatic, bulky amino acids.

| I | II | III | IV | V |
|---|----|-----|----|---|
| A | N | H | M | F |
| S | D | R | L | Y |
| T | E | K | I | W |
| P | Q |   | V |   |
| G |   |   | C |   |

In some embodiments, a polypeptide of the invention may comprise functional fragments or variants of a BAFF specific binding moiety of the invention that have, at most, 20, 15, 10, 9, 8, 7, 6, 5, 4, 3, 2, or 1 amino acid substitutions compared to a polypeptide sequence recited herein, as long as it retains measurable biological activity alone or as a component of a BAFF antagonist compound. A polypeptide of the invention may further be with or without a signal sequence. In certain embodiments, the retained activity is at least 50% that of the BAFF binding moiety according to Table 1.

In some embodiments, a polypeptide of the invention shares at least 85%, 90%, 95%, 96%, 97%, 98%, 99% or more amino acid sequence identity to any one of the amino acid sequences of FW1, FW2-3, FW4, CDR1 or CDR3 of Table 1, as long as it retains measurable biological activity alone or as a component of a BAFF antagonist compound. In certain embodiments, the retained activity is at least 50% that of the BAFF binding moiety according to Table 1.

BAFF specific VNAR comprising compounds of the invention may optionally be conjugated to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like The invention further provides methods of making derivatives of BAFF specific VNARs of the invention using biochemical engineering techniques well known to those of skill in the art. Such derivatives include, inter alia, multivalent or multispecific molecules comprising a BAFF specific binding moiety, including immunoconjugates. A large body of art is available relating to how to make and use antibody drug conjugates. Such knowledge and skill in the art may be adapted for use with the BAFF specific binding moieties and BAFF antagonist compounds of the invention. See, e.g., WO2007/140371; WO2006/068867 specific to BAFF; methods relating to making and/or using different ligand antagonist conjugates may be applied. In certain embodiments, the BAFF selective binding moieties and antagonist compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Pharmaceutical Compositions

The present invention further provides pharmaceutical compositions comprising a BAFF specific binding moiety or compound, or a pharmaceutically acceptable salt or solvate thereof, according to the invention, together with a pharmaceutically acceptable carrier, excipient or vehicle.

Accordingly, the present invention further provides a pharmaceutical composition comprising a BAFF specific binding moiety or a BAFF antagonist compound comprising a BAFF specific binding moiety, as well as variant and derivative compounds comprising a BAFF specific binding moiety of the invention. Certain embodiments of the pharmaceutical compositions of the invention are described in further detail below.

The present invention also provides pharmaceutical compositions comprising a BAFF specific binding moiety or a BAFF antagonist compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Nucleic Acid Sequences that Encode a BAFF Selective Binding Moiety or BAFF Antagonist Compound In one aspect, the invention provides an isolated nucleic acid which encodes a BAFF specific binding moiety or BAFF antagonist compound of the invention, or a fragment or derivative thereof. The nucleic acid may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of Table 1. The invention also provides an isolated nucleic acid molecule comprising a sequence that hybridizes under stringent conditions to a nucleic acid sequence which encodes a BAFF specific binding moiety or BAFF antagonist compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a polypeptide or fragment thereof having CDR 1, CDR3 or framework amino acid sequences shown in Table 1, and variants thereof according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode BAFF specific binding moiety proteins or biologically active portions thereof. Also included are nucleic acid fragments sufficient for use as hybridization probes to identify BAFF binding moiety encoding nucleic acids and fragments for use as polymerase chain reaction (PCR) primers for the amplification or mutation of BAFF specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention, e.g., a nucleic acid molecule encoding any one of the amino acid sequences disclosed in Table 1, or a complement of any of these nucleotide sequences, may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a BAFF selective binding moiety or BAFF antagonist compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. Also included are nucleic acid molecules capable of hybridizing to the complement of a sequence encoding the proteins of the invention under stringent or moderately stringent conditions (see, e.g., Ausubel, et al., CURRENT PROTOCOLS IN MOLECULAR BIOLOGY, John Wiley & Sons, New York, N.Y., 1993, and below). An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing BAFF Specific VNAR Binding Moieties and BAFF Antagonists Comprising them.

The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a BAFF antagonist compound using standard solid-phase or liquid-phase methodology, either stepwise or by fragment assembly, and isolating and purifying the final peptide compound product; (2) expressing a nucleic acid construct that encodes a polypeptide or polypeptide component of a BAFF antagonist compound in a host cell and recovering the expression product from the host cell or host cell culture; or (3) cell-free in vitro expression of a nucleic acid construct encoding a polypeptide or polypeptide component of a BAFF antagonist compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a BAFF antagonist compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a BAFF specific binding polypeptide of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

BAFF antagonist compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Diefenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce BAFF antagonists of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a BAFF antagonist compound of the invention can be accomplished using standard techniques known in the art. Mammalian cells are preferred host cells for expression of peptide antagonists. Particularly useful mammalian cells include, inter alia, HEK 293, NSO, DG-44, and CHO cells, but any other suitable host cell may be used according to the invention. Preferably, the BAFF antagonist compounds are secreted into the medium in which the host cells are cultured, from which the BAFF antagonist compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a BAFF antagonist compound of the invention.

Methods of Detection

In certain embodiments, the BAFF antagonist compounds of the invention may be used to detect and quantify levels of BAFF, or cells that express BAFF-R. This can be achieved, for example, by contacting a test sample (such as an in vitro sample) and a control sample with a BAFF specific binding moiety of the invention, or a BAFF antagonist compound comprising it, under conditions which permit formation of a complex between the antagonist and BAFF, or between BAFF and BAFF-R, or both. Any bound BAFF complexes are detected and/or quantified in BAFF specific VNAR containing samples and control samples.

Accordingly, the invention further provides methods for detecting the presence of BAFF or BAFF-R in a sample, or measuring the amount of either of the foregoing, comprising contacting the sample, and preferably a control sample, with a BAFF antagonist compound of the invention under conditions that permit complex formation between the BAFF binding moiety of the antagonist and BAFF, e.g., human BAFF. Formation or inhibition of formation of a BAFF/BAFF-R complex is then detected and/or quantified. A variety of tests can be designed based on features of binding or competition for binding. For example, the presence of BAFF-R in a test sample may be detected directly, or may be detected and quantified based on the ability to compete for binding of BAFF-R by BAFF. In general, the difference in complex formation between a test sample and a control sample is indicative of a binding interaction.

Kits for Detecting or Quantifying BAFF in a Sample

Also within the scope of the invention are kits comprising at least one BAFF specific binding moiety or BAFF antagonist compound or composition of the invention, and optionally, instructions for use. Kits may be useful for quantifying BAFF or BAFF-R in a sample, or may be useful for detection of BAFF, such as in diagnostics methods. The kit may further or alternatively comprise at least one nucleic acid encoding a BAFF specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring BAFF in a sample or in a subject, or for diagnosing whether a patient belongs to a group that responds to a BAFF antagonist which makes use of a compound, composition or related method of the invention as described herein.

BAFF Antagonists and Compositions for Use in Methods of Medical Treatment

The present invention provides a BAFF antagonist compound for use, alone or in combination with one or more additional therapeutic agents in a pharmaceutical composition, for treatment or prophylaxis of conditions, diseases and disorders responsive to modulation (such as inhibiting or blocking) of the interaction between BAFF-R and BAFF.

BAFF antagonist compounds and pharmaceutical compositions of the invention may be used in the treatment of a variety of conditions, disorders or diseases involving B cells. Treatment of with a BAFF antagonist compound of the invention preferably leads to in vivo B cell depletion. As such, BAFF antagonist compounds of the invention, and compositions comprising them, will be useful in methods for treating a variety of pathological disorders in which killing or depleting B cells may be beneficial, such as, inter alia, systemic lupus erythematosus, rheumatoid arthritis, multiple sclerosis and certain other autoimmune disorders or diseases, and e.g., lymphomas, leukemias and myelomas. The present invention provides methods for suppressing B cell proliferation, and treating B cell disorders, including neoplasms, tumors and other malignancies, comprising the step of administering to a subject in need thereof a therapeutically effective amount of a BAFF antagonist compound.

In general, B-cell disorders may be classified as defects of B cell development and/or immunoglobulin production (immunodeficiencies) and/or excessive or uncontrolled B cell proliferation (e.g., in leukemias, lymphomas and myelomas). As used herein, a "B cell disorder" is intended to refer to both types of disease, unless otherwise indicated by context.

The invention thus provides methods of treatment or prevention of a B cell associated disorder, the method comprising the step of administering to a subject (e.g., a patient) in need thereof a therapeutically effective amount of the BAFF antagonist compound or pharmaceutical composition comprising a BAFF antagonist compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, Pa., 2005.

In certain embodiments, BAFF antagonists and pharmaceutical compositions of the invention may be used to treat or prevent inflammatory conditions, including but not limited to rheumatoid arthritis (RA), multiple sclerosis (MS), psoriasis, Type 1 diabetes mellitus, scleroderma/systemic sclerosis, Sjögren's syndrome (SS), systemic lupus erythematosus (SLE), certain forms of thyroiditis, certain forms of uveitis, vitiligo, granulomatosis with polyangiitis (Wegener's) alopecia areata, autoimmune hemolytic anemia, autoimmune hepatitis, dermatomyositis, certain forms of juvenile idiopathic arthritis, (acute) glomerulonephritis, Graves' disease, Guillain-Barré syndrome, idiopathic thrombocytopenic purpura (ITP), myasthenia gravis, some forms of myocarditis, pemphigus/pemphigoid, pernicious anemia, polyarteritis nodosa, polymyositis, primary biliary cirrhosis.

In certain embodiments, the present invention provides methods for treating B cell malignancies or neoplasms and other blood cell associated cancers in a mammalian subject, such as a human, the method comprising the step of administering to a subject in need thereof a therapeutically effective amount of a BAFF antagonist compound or pharmaceutical composition comprising a BAFF antagonist compound. In some embodiments, a BAFF antagonist compound of the invention is used to treat a B cell-, plasma cell- or antibody-mediated disease or disorder, such as for example Multiple Myeloma (MM), chronic lymphocytic leukemia (CLL), non-secretory multiple myeloma, Smoldering multiple myeloma, Monoclonal gammopathy of undetermined significance (MGUS), Solitary plasmacytoma (Bone, Extramedullar), Lymphoplasmacytic lymphoma (LPL), Waldenstrom's Macroglobulinemia, Plasma cell leukemia, Primary Amyloidosis (AL), Heavy chain disease, POEMS syndrome/osteosclerotic myeloma, Type I and II cryoglobulinemia, Light chain deposition disease, Goodpasture's syndrome, Pemphigus and Pemphigoid disorders, and Epidermolysis bullosa acquisita; or any Non-Hodgkin's Lymphoma B-cell leukemia or Hodgkin's lymphoma (HL) with BAFF-R expression or any conditions associated with the development of neutralizing antibodies to recombinant protein replacement therapy.

BAFF antagonist compounds and compositions of the invention may be beneficial in treating or diagnosing certain B-cell neoplasms. B cell malignancies or neoplasms that may be diagnosed or treated using the methods described herein include, but are not limited to, Non-Hodgkin's Lymphomas (NHL), Diffuse Large B Cell Lymphoma (DLBCL), Small lymphocytic lymphoma (SLL/CLL), Lymphoplasmacytoid lymphoma, Mantle cell lymphoma (MCL), Follicular lymphoma (FL), Marginal zone lymphoma (MZL), Extranodal mucosa-associated lymphoid tissue lymphoma (MALT lymphoma), Nodal (Monocytoid B-cell lymphoma), Splenic, Diffuse large cell lymphoma, Burkitt's lymphoma, Lymphoblastic lymphoma, precursor B-lymphoblastic leukemia, B-cell chronic lymphocytic leukemia, Solitary Plasmacytoma (Bone, Extramedullar), Multiple Myeloma (MM), and Smoldering Multiple Myeloma (SMM). Treatment and diagnosis of other B-cell neoplasms are also considered to fall within the scope of the present invention.

In certain embodiments, an autoimmune disease or cancer to be treated using a BAFF antagonist compound or composition according to the invention is selected from (a) Systemic Lupus Erythematosus; (b) Rheumatoid Arthritis; (c) Multiple Sclerosis; (d) Idiopathic Thrombocytopenic Purpura; (e) Sjogren's syndrome; (f) Diabetes; (g) Waldenstrom's macroglobulinaemia; (h) acute lymphocytic leukemia; (i) chronic lymphocytic leukemia; (j) non-Hodgkin's lymphoma; (k) multiple myeloma; (l) vasculitis; and (m) graft or transplant rejection.

In certain embodiments, the condition, disease or disorder is selected from Multiple Myeloma (MM), Smoldering Multiple Myeloma (SMM), Chronic Lymphocytic Leukemia (CLL), Solitary Plasmacytoma (Bone, Extramedullar), Waldenstrom's Macroglobulinemia and Idiopathic thrombocytopenic purpura (ITP).

The BAFF antagonist compounds and related compositions of the invention may be used in the manufacture of a pharmaceutical composition or medicament for the treatment of one or more of each of the B cell related conditions, diseases and disorders described herein.

Formulations, Administration and Dosing

BAFF antagonist compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Exemplary pH buffering agents include phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different BAFF antagonist compounds of the invention, or a VNAR sequence containing, BAFF specific binding region thereof, or an ester, salt or amide of any of the foregoing, and at least one pharmaceutically acceptable carrier. Such compositions may include one or more different BAFF specific binding moieties or compounds in combination to produce an immunoconjugate or multispecific molecule comprising at least one BAFF specific binding moiety. For example, a pharmaceutical composition of the invention may comprise a combination of BAFF specific binding moieties which bind to different epitopes of BAFF or which otherwise have complementary biological activities.

Pharmaceutical compositions of the invention may be administered alone or in combination with one or more other therapeutic or diagnostic agents. A combination therapy may include a BAFF antagonist compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion).

Depending on selected route of administration, the BAFF specific binding moiety comprising compound or component may be coated in a material or materials intended to protect the compound from the action of acids and other natural inactivating conditions to which the active BAFF binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

BAFF antagonist compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active BAFF antagonist compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a BAFF specific binding moiety (or a BAFF antagonist compound comprising such a moiety) in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a BAFF antagonist compound of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a BAFF antagonist compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. BAFF antagonist compounds will typically be administered on multiple occasions. Intervals between single dosages can be, for example, 2-5 days, weekly, monthly, every two or three months, every six months, or yearly. Intervals between administrations can also be irregular, based on regulating blood levels of BAFF antagonist to the target BAFF ligand in the subject or patient. In some methods, dosage is adjusted to achieve a plasma antagonist concentration of about 1-1000 µg/ml and in some methods about 25-300 µg/ml. Dosage regimens for a BAFF antagonist of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more BAFF antagonist compounds with different binding properties may be administered simultaneously or sequentially, in which case the dosage of each administered antagonist may be adjusted to fall within the ranges described herein.

In certain embodiments, a BAFF antagonist compound of the invention may be administered as a sustained release formulation, in which case less frequent administration is required. Dosage and frequency vary depending on the half-life of the BAFF antagonist in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the BAFF antagonist compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular BAFF antagonist compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a BAFF antagonist compound of the invention may result in a decrease in severity of disease symptoms, an increase in frequency and duration of disease symptom-free periods, or a prevention of impairment or disability due to the disease affliction.

A BAFF antagonist compound or composition of the present invention may be administered via one or more routes of administration, using one or more of a variety of methods known in the art. As will be appreciated by the skilled worker, the route and/or mode of administration will vary depending upon the desired results. Routes of administration for BAFF antagonist compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrastemal injection and infusion.

In other embodiments, a BAFF antagonist compound or composition of the invention may be administered by a non-parenteral route, such as a topical, epidermal or mucosal route of administration, for example, intranasally, orally, vaginally, rectally, sublingually or topically.

As described elsewhere herein, an active BAFF antagonist compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic BAFF antagonist composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the BAFF antagonist compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Delivery Devices and Kits

In certain embodiments, the invention relates to a device comprising one or more BAFF antagonist compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

EXAMPLES

The following examples demonstrate certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. Nurse Shark Semi-Synthetic Library

For the purposes of the present invention, any method in the art for making a nurse shark library may be used. In the following examples, a nurse shark semi-synthetic library (complexity=$1.6 \times 10^{10}$ cfu) was constructed. In brief, a vector capable of use in phage display and in monomeric VNAR expression was constructed. The vector was a modified version of pSEX81 (Progen) in which a 6× His tag (SEQ ID NO: 42), a FLAG tag, and an amber stop codon were inserted between the VNAR sequences and the full-length PIII protein of the M13 phage. VNAR sequences were inserted into a restriction site engineered downstream from the PelB signal sequence of pSEX81 using oligonucleotides by the Quickchange method.

Example 2. Selection of BAFF-Binding VNARs

Selection of BAFF-interacting VNARs displayed as a fusion of the PIII protein on M13 bacteriophage was performed essentially as described in Griffiths et al. 1994, *EMBO J.*, 13:3245-3260. Briefly, human BAFF (Prospec) was immobilized on Nunc Maxisorp 96-well plates and exposed to an excess (about 100 times the library size) of phages rescued from the OsX-3 library. After incubating for 1.5 hours at room temperature, unbound particles were removed by washing, first in PBS-0.1% Tween, then in PBS. The bound phages were subsequently eluted with triethylamine (100 mM) and quickly neutralized in Tris (pH=7.5). Eluted particles were then used to infect *E. coli* ER2738. A portion of the culture was used to estimate the titer of eluted phages (by counting the number of antibiotic-resistant colonies), the rest of the culture was infected with M13KO7 helper phage to produce phages for the next round of selection. Four rounds of selection were performed using increasingly stringent conditions consisting in progressively reducing the coated BAFF concentration at every round (50, 5, 2.5, and 1 µg/mL respectively), and increasing the washing steps from 10 to 20.

Each of the four input phage populations was tested for specificity to BAFF by polyclonal phage ELISA. Briefly, $10^{12}$ phages were incubated in Nunc Maxisorp 96-well plates coated at 1 µg/mL with either BAFF-Fc (Sino Biological) or HSA (Sigma). After incubating for 1 hour at room temperature, unbound particles were removed by washing the wells three times in PBS-0.1% Tween-20. Bound bacteriophages were then detected using a specific anti-M13 antibody (GE) (FIGS. 5-7).

Screening for BAFF-R Binding Clones

After selection rounds three and four, 93 individual clones were picked and grown in 96 deep-well plates in auto-induction medium (Novagen). Periplasmic protein was extracted by osmotic shock as described in Müller M R et al. (Generation and isolation of target-specific single-domain antibodies from shark immune repertoires. *Methods Mol Biol.* 2012; 907:177-94) and directly used in a binding ELISA. Briefly, Nunc Maxisorp 96-well plates were coated at 1 µg/mL with either BAFF-Fc or HSA and periplasmic fraction, pre-blocked in PBS-0.1% Tween+2.5% milk, was exposed to the coated surface. After washing in PBS-0.1% Tween, bound VNARs were detected using a peroxidase-conjugated anti-FLAG antibody (Sigma). Absorbance at 450 nm was recorded using an Envision multiwell reader (Perkin Elmer) and BAFF-specific clones were selected using the criteria: BAFF signal/HSA signal≥4. The DNA sequence of positive clones was determined by the Sanger chain termination method (GATC biotech), using the specific oligonucleotide 5'-tcattaggcaccccaggctttacac-3'. Protein alignments were performed using the BioEdit software.

Screening for BAFF-R Blocking Clones

The ability of selected BAFF-specific VNARs to prevent the binding of BAFF to its receptor (BAFF-R) was tested in a blocking ELISA format. Briefly, selected clones were grown in 96 deep-well plates and the periplasmic fraction was extracted as described above. Nunc Maxisorp 96-well plates were coated at 1 µg/mL with the BAFF-R extracellular domain (Peprotech) and blocked in PBS-0.1% Tween+2.5% milk. The periplasmic fraction was also pre-blocked in PBS-0.1% Tween-20+2.5% milk in the presence of 1.14 nM BAFF-Fc (Sino Biological) before being exposed to the BAFF-R coated surface. After washing in PBS-0.1% Tween-20, BAFF bound to its receptor was detected via its Fc moiety using a peroxidase-conjugated anti-human Fc (Sigma). Absorbance at 450 nm was recorded using an Envision multiwell reader (Perkin Elmer) (FIG. 8) and clones reducing the amount of BAFF bound to its receptor by more than 50% were selected as specific blockers.

Example 3. Expression and Purification of Monomeric BAFF Specific VNARs

Selected BAFF-binding clones were expressed at larger scale in order to purify monomeric VNARs for biochemical analysis. 500 mL-cultures were grown in auto-induction medium (Novagen) and periplasmic fraction was extracted by osmotic shock by resuspending the bacteria in TES buffer (50 mM Tris, 1 mM EDTA, 20% Sucrose w/v) mixed with an equal volume of TES diluted 1:5 in water. After 30 minutes on ice, the lysate was clarified by centrifugation and the salt concentrations were adjusted to 500 mM NaCl and 10 mM imidazole in 1×PBS. The periplasmic fraction was then purified on Nickel-Sepharose resin (Qiagen), washed in 1×PBS, 10 mM imidazole, 500 mM NaCl, and then eluted in 1×PBS, 500 mM imidazole, 500 mM NaCl. The purified protein was then buffer-exchanged against PBS and concentrated by centrifugation with Vivaspin 20 filters (Sartorius, MWCO 5000). Endotoxin was subsequently removed from the protein sample using VivaPure Q mini column (Sartorius) and the protein was sterile filtered (0.22 µm). After estimating the protein concentration using Bradford reagent (Pierce), the purified protein was frozen in aliquots.

Determining Biochemical EC50 Values

Figure 9:
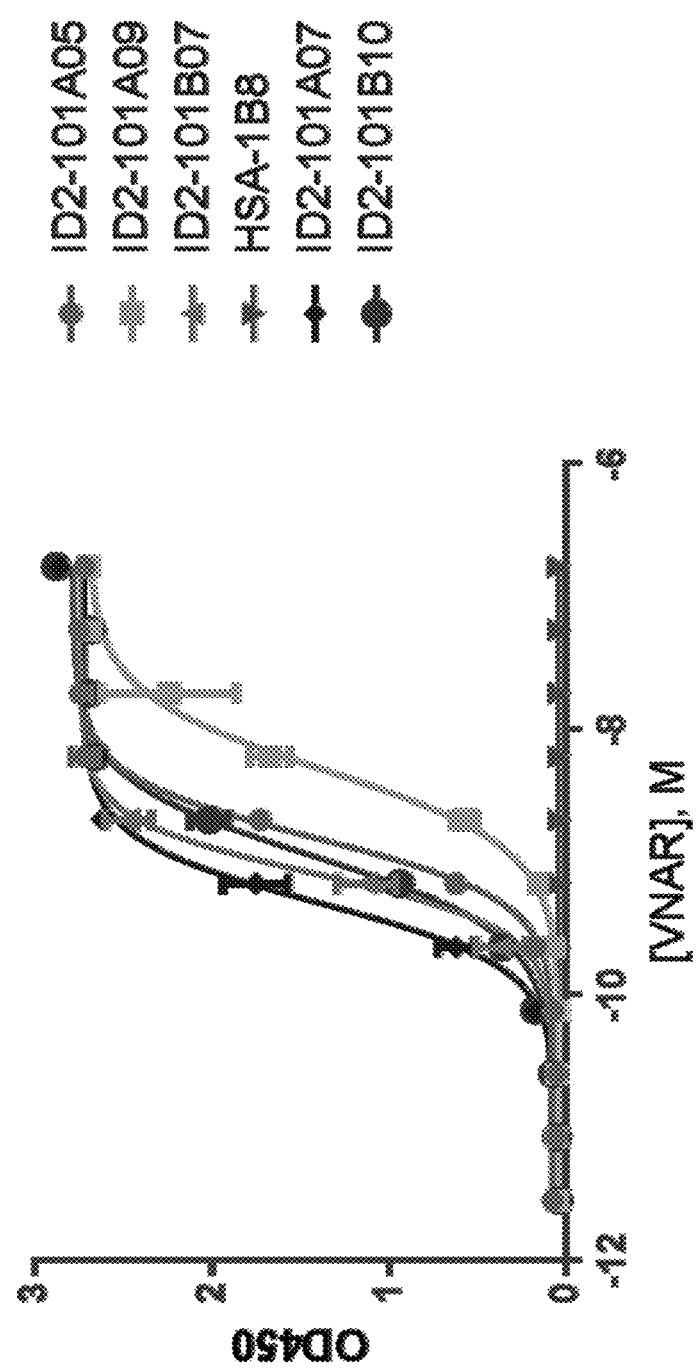
FIG. 9 shows EC50 curves of five selected clones. HSA-1B8 is a non-specific VNAR used as a negative control (see Example 3).

The biochemical EC50 (equilibrium constant, the concentration at which the ratio of bound to unbound is 50:50) of selected clones was determined by serially diluting purified monomeric VNARs in blocking buffer (PBS-0.1% Tween+2.5% milk) and exposing it to preblocked Nunc Maxisorp 96-well plates coated at 1 µg/mL with BAFF-Fc (Sino Biological). After washing in PBS-0.1% Tween-20, bound VNARs were detected using a peroxidase-conjugated anti-FLAG antibody (Sigma). Absorbance at 450 nm was recorded using an Envision multiwell reader (Perkin Elmer) (FIG. 9) and EC50s were calculated by fitting curves (non-linear regression) using GraphPad Prism®.

Determining Biochemical IC50 Values

Figure 10:
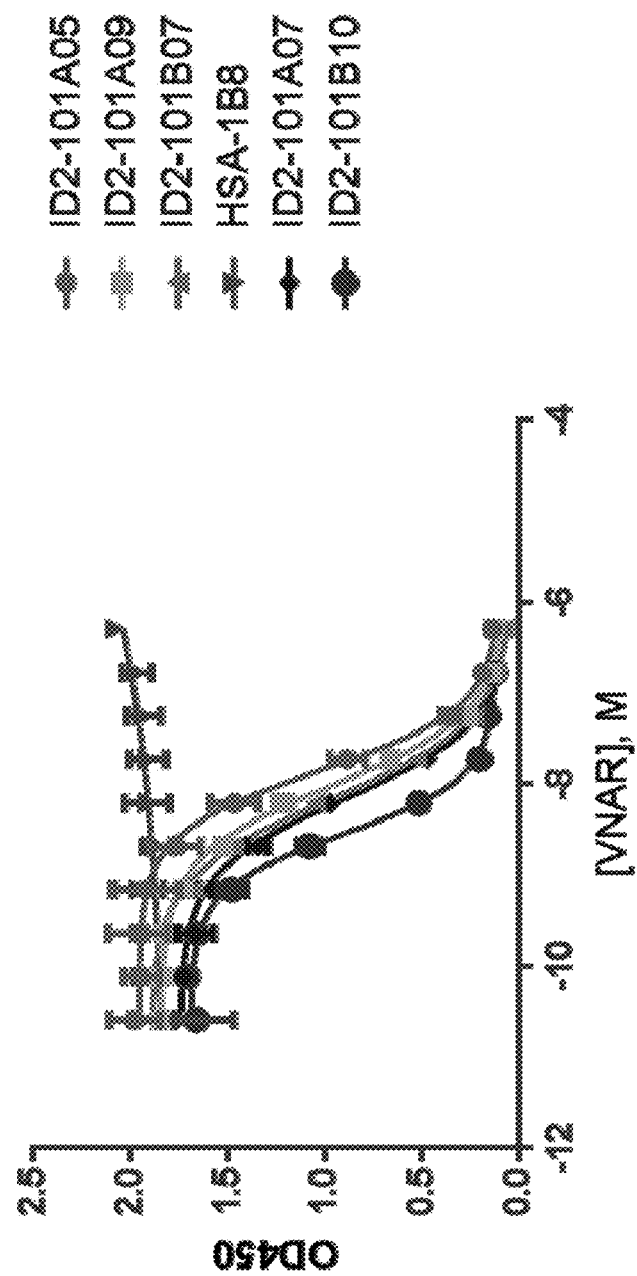
FIG. 10 shows IC50 curves of five selected clones. HSA-1B8 is a non-specific VNAR used as a negative control (see Example 3).

The biochemical IC50 (inhibition constant, the concentration which inhibits binding of one agent to another agent by 50%) of selected clones was determined by serially diluting purified monomeric VNARs in blocking buffer (PBS-0.1% Tween-20+2.5% milk) supplemented with 1.14 nM BAFF-Fc. The pre-blocked proteins were then exposed to Nunc Maxisorp 96-well plates were coated at 1 µg/mL with the BAFF-R extracellular domain, preblocked in (PBS-0.1% Tween+2.5% milk). After washing in PBS-0.1% Tween, BAFF bound to its receptor was detected via its Fc moiety using a peroxidase-conjugated anti-human Fc (Sigma #A0170). Absorbance at 450 nm was recorded using an Envision multiwell reader (Perkin Elmer) (FIG. 10) and IC50 values were calculated by fitting the curves (non-linear regression) using GraphPad Prism®.

Example 4. Measuring BAFF VNAR Binding Affinities

Surface Plasmon Resonance provides a definitive measure of the affinity of an interaction and may be used to measure affinity of binding by a BAFF binding moiety or BAFF antagonist compound of the invention to a selected target compound, such as human BAFF, mouse or mammalian non-human BAFF, or a putative cross reactive compound such as APRIL. Specific VNARs of the invention were immobilized on flow cells at a density of approximately 500 RUs. Recombinant BAFF was then applied in the fluid phase at a flow rate of 20 µl/min with association for 2 minutes, followed by dissociation for 30 minutes at a range of at least 6 concentrations from 1 µM to 1 pM. The sensorgrams were then modeled to determine the kinetic properties of the interaction including rate of association, dissociation and the affinity of the interaction.

Example 5. Murine Splenocyte In Vitro Proliferation Assay

Figure 11:
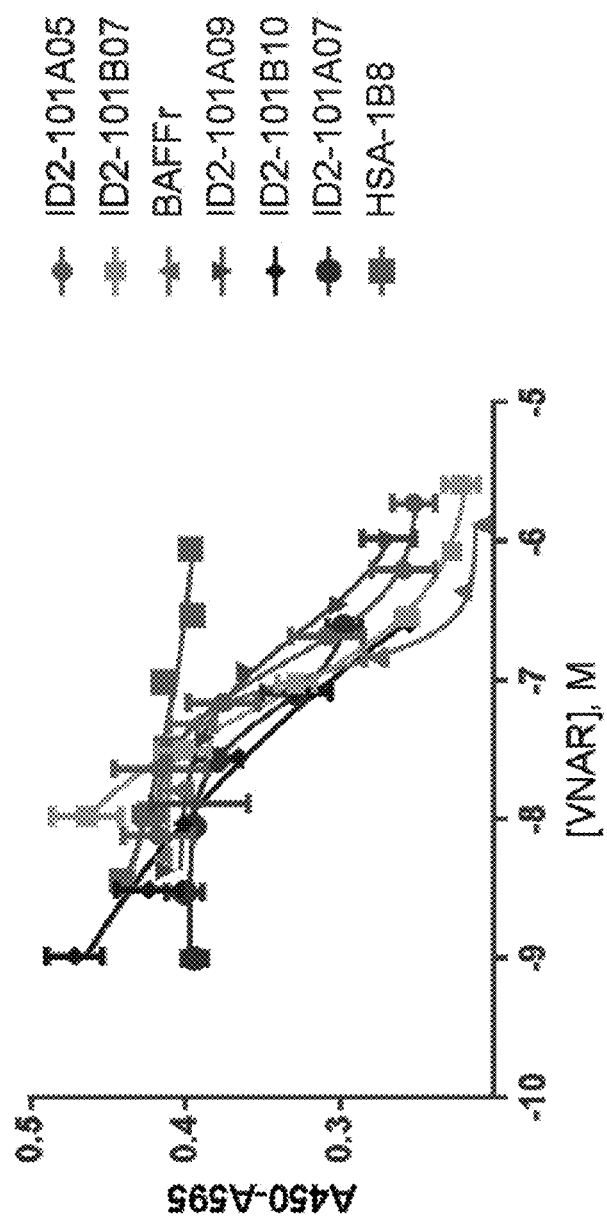
FIG. 11 shows inhibition of BAFF bioactivity in mouse splenocytes. The results depict the cellular IC50 curves of the five best inhibitors of BAFF bioactivity. HSA-1B8 is a non-specific VNAR used a negative control (see Example 5).

Mouse splenocytes were obtained by dissociating spleens of C57BL/6 mice on a 70 µm cell strainer and lysing red blood cell in RBC buffer (Sigma). B cells were then purified by depleting CD43-positive cells using magnetic microbeads (Miltenyi Biotec) according to manufacturer's instructions. The obtained B cells were subsequently stimulated with goat anti-mouse IgM antibody (Jackson Laboratories) at 10 µg/mL final assay concentration. Recombinant VNARs were serially-diluted and pre-complexed with recombinant BAFF-Fc at 5 ng/mL final assay concentration in RPMI 1640 supplemented with 10% FBS, for 30 minutes at 37° C. Stimulated B cells were added to the pre-complexed proteins and further incubated for 72 hours at 37° C., 5% $CO_2$. Cell proliferation was then estimated by incubating cells with WST-1 reagent (Roche) and reading absorbance at 450 nM, subtracting a reference wavelength at 595 nM (FIG. 11). IC50 values were calculated by fitting the curves (non-linear regression) using GraphPad Prism®.

Example 6. VNARs that Block the Interaction Between BAFF and TACI or BCMA

Figure 12:
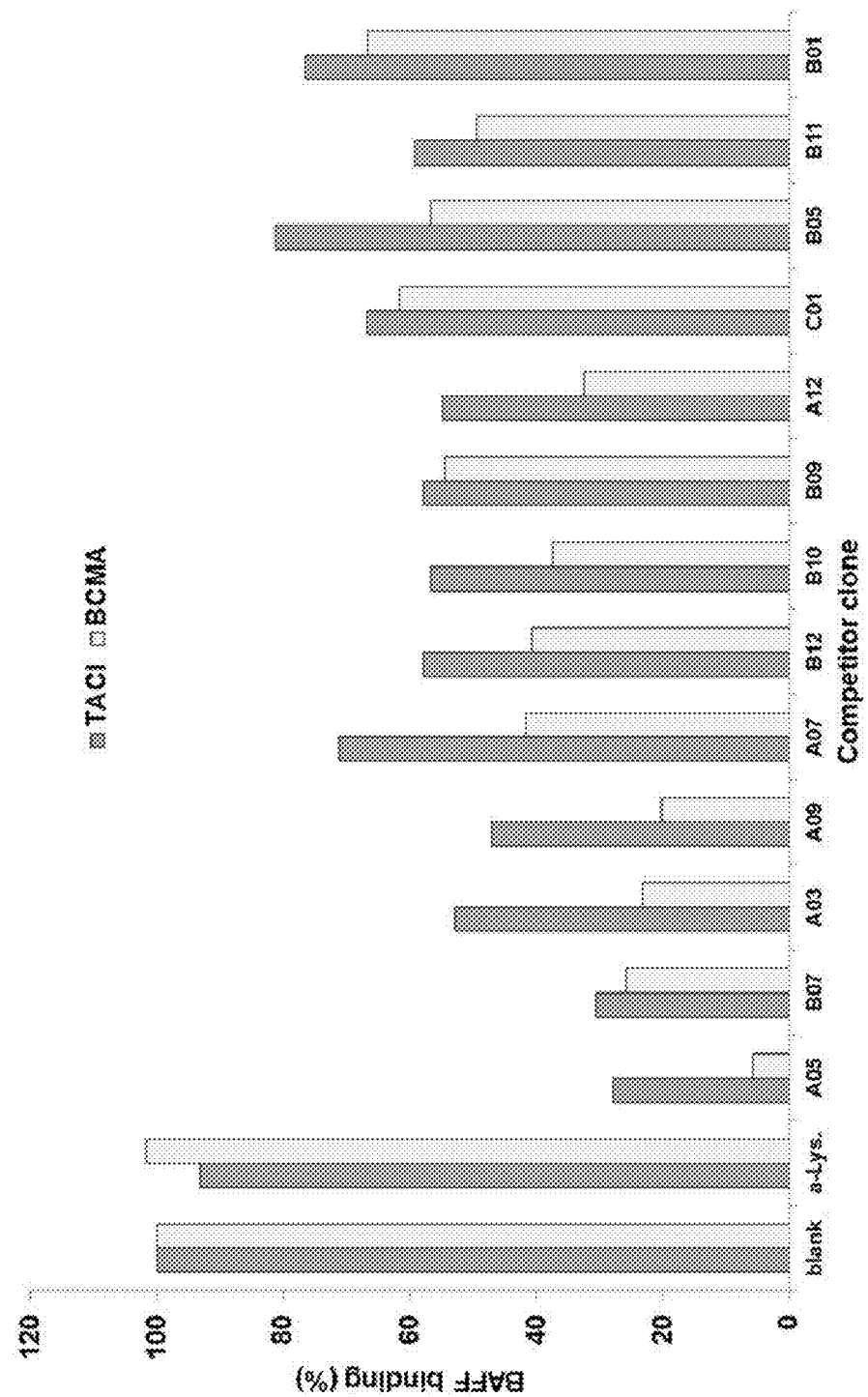
FIG. 12 shows the ability of periplasmic protein extracts from thirteen different VNAR clones to block BAFF binding to the TACI (dark gray) and BCMA (light gray) receptors as tested by ELISA (see Example 6). All tested VNAR clones block the interaction between BAFF and both receptors compared to a negative VNAR control (a-Lys) or to a test sample with no added VNAR (blank).

The ability of BAFF/BR3 (BAFFr) blocking clones to also block the interaction between BAFF and its other two receptors (TACI and BCMA) were tested in a blocking ELISA format. Briefly, selected clones were grown in a 96 deep-well format and periplasmic fractions were extracted as previously described. Nunc Maxisorp 96 well plates were coated at 1 µg/mL with either TACI or BCMA (Peprotech) and blocked in PBS-0.1% Tween+2.5% Milk. The periplasmic fraction was also pre-blocked in PBS-0.1% Tween+2.5% Milk in the presence of 0.5 nM BAFF-Fc (Sino Biological) before being exposed to the receptor-coated surface. After washing in PBS-0.1% Tween, BAFF bound to its receptor was detected via its Fc moiety using a peroxidase-conjugated anti-human Fc (Sigma). Absorbance at 450 nm was recorded using an Envision multiwell reader (Perkin Elmer). The results are shown in FIG. 12. Results showed that as compared to a negative control VNAR anti-Lysosyme (a-Lys), the thirteen tested clones appeared to block the interaction between BAFF and both TACI and BCMA.

Example 7. VNAR Binding Specificity for BAFF Relative to APRIL

Figure 13:
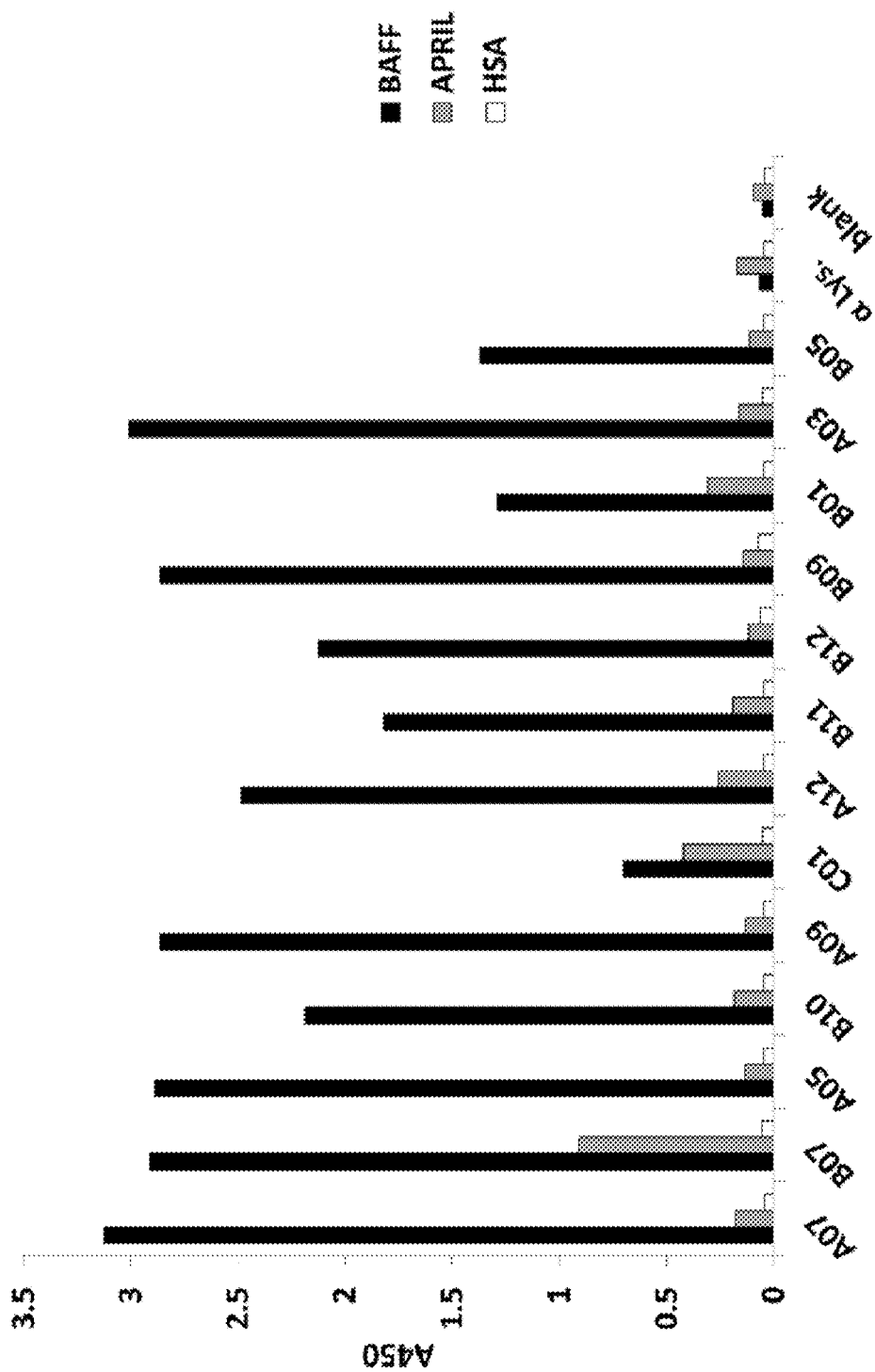
FIG. 13 shows the ability of periplasmic protein extracts from thirteen different VNAR clones to bind directly to either BAFF-Fc (black bars), a related TNF family ligand, APRIL (gray bars) or human serum albumin (HSA; white bars), as tested by ELISA (see Example 7). With the exception of B07, which showed weak cross-reactivity, all other VNAR clones appear to bind specifically to BAFF.

Clones blocking the interaction between BAFF and its three receptors were tested for their ability to cross-react with BAFF's closest related protein, APRIL. Clones were grown in a 96 well format, periplasmic fraction was extracted by osmotic shock as previously described and directly used in a binding ELISA. Nunc Maxisorp 96 well plates were coated at 1 µg/mL with either BAFF-Fc (Sino Biological), HSA (Sigma), or APRIL (Sigma) and periplasmic fraction, pre-blocked in PBS-0.1% Tween+2.5% Milk, was exposed to the coated surface. After washing in PBS-0.1% Tween, bound VNARs were detected using a peroxidase-conjugated anti-FLAG antibody (Sigma). Absorbance at 450 nm was recorded using an Envision multiwell reader (Perkin Elmer). As shown in FIG. 13, with the exception of B07 which showed a slight binding to APRIL, all the blocker clones appeared specific to BAFF.

Example 8. Epitope Binning of BAFF-Binding VNARs

Figure 14:
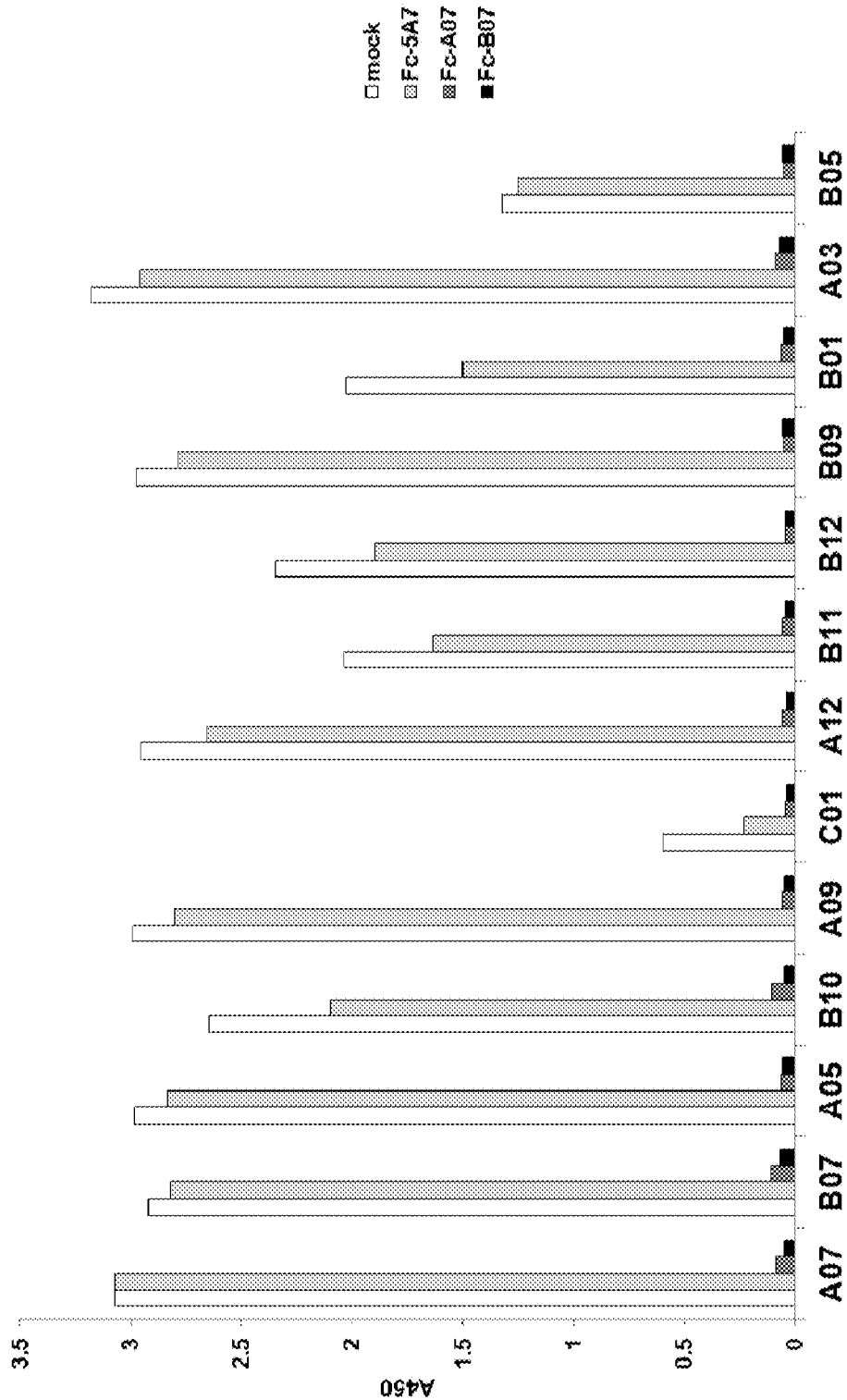
FIG. 14 shows the ability of periplasmic protein extracts from thirteen different VNAR clones to compete for binding with VNARs formatted as Fc fusions, as tested by ELISA (see Example 8). Each VNAR clone was tested against two VNAR clones formatted as Fc fusions: Fc-A07 (dark gray bars) and Fc-B07 (black bars). Fc-5A7 (an unrelated Fc fusion; light gray bars) does not compete for BAFF binding and was comparable to the mock control (white bars). Every BAFF specific VNAR clone was competed by both A07 and B07 Fc fusions but not by the negative control (Fc-5A7), indicating that all of the VNARs target a similar or overlapping epitope on BAFF.

In order to group the blocking clones into different categories based on the epitope that each one recognizes on the BAFF proteins, Nunc Maxisorp 96 well plates were coated at 1 µg/mL with recombinant BAFF (Sino biologicals). Clones were grown in a 96 well format and periplasmic fraction was extracted by osmotic shock as previously described. The periplasmic fraction was then pre-blocked in PBS-0.1% Tween+2.5% Milk in the presence of a competitor VNAR-Fc molecule at 2 µM final concentration. Two anti-BAFF VNAR-Fcs were used in this assay (A07, B07) as well as a negative control lysozyme-binding VNAR (5A7). The pre-blocked fraction was then exposed to the coated surface, and after washing in PBS-0.1% Tween, bound VNARs were detected using a peroxidase-conjugated anti-FLAG antibody (Sigma). Absorbance at 450 nm was recorded using an Envision multiwell reader (Perkin Elmer). The results are shown in FIG. 14. Results showed that the binding of each clone to BAFF was competed by both A07 and B07, revealing that all the clones of the selected panel of blockers target the same (or at least an overlapping) epitope on BAFF.

Example 9. IC50s of Selected VNARs for TACI and BCMA

Figure 15:
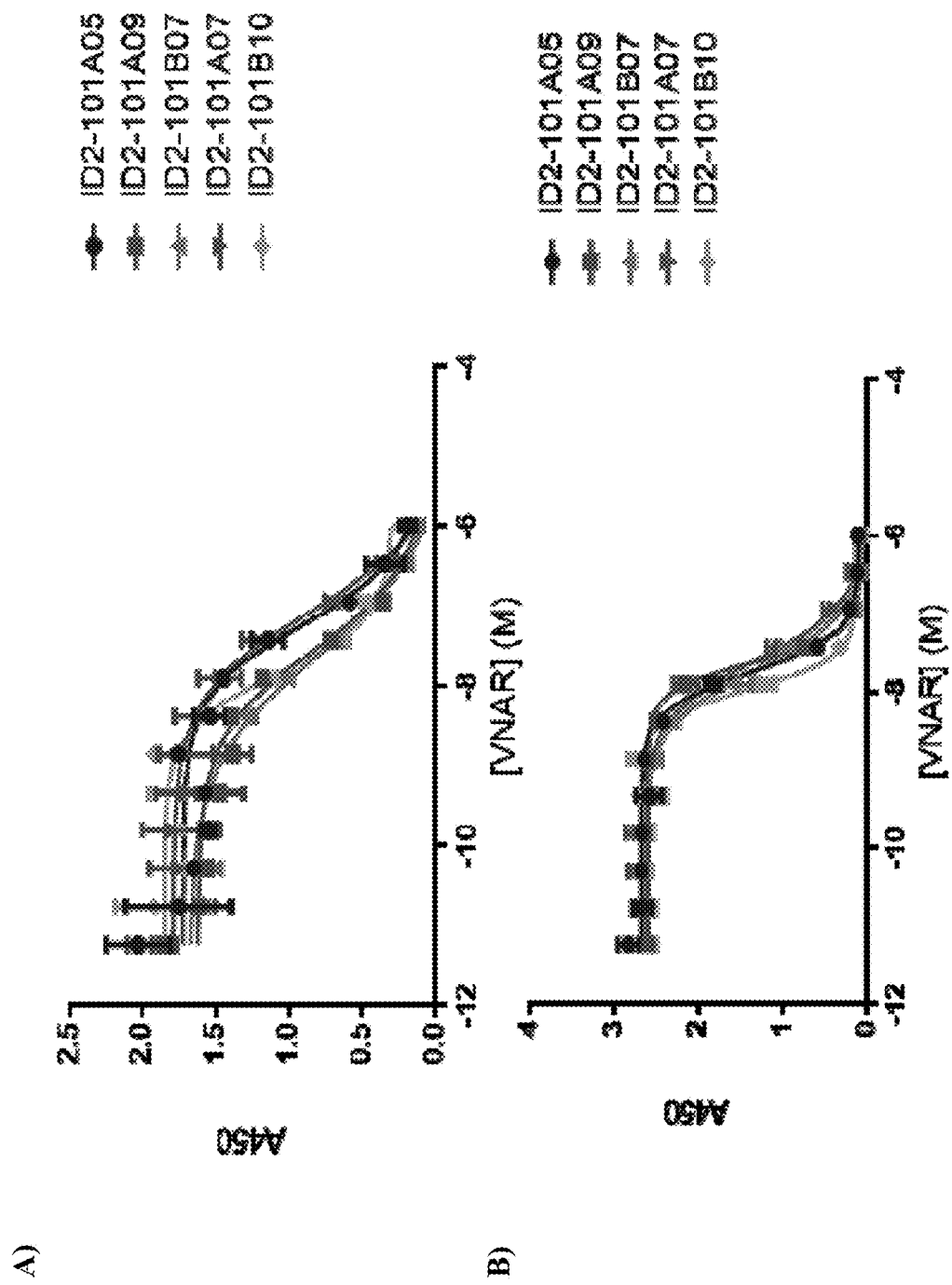
FIGS. 15A-B shows biochemical IC50 curves of five different VNAR monomers (ID2-101A05, -101A09, -101B07, -101A07, and -101B10) serially diluted in the presence of constant (0.5 nM) BAFF-Fc and their ability to bind to (A) TACI and (B) BCMA receptors compared to BAFFr (BR3) (see Example 9).

The biochemical IC50 for each of the five main lead molecules was determined on both TACI and BCMA by serially diluting purified monomeric VNARs in blocking buffer (PBS-0.1% Tween+2.5% Milk) supplemented with 0.5 nM BAFF-Fc (Sino Biological). The pre-blocked proteins were then exposed to Nunc Maxisorp 96 well plates which were coated at 1 µg/mL with the recombinant human TACI or BCMA (Peprotech), preblocked in (PBS-0.1% Tween+2.5% Milk). After washing in PBS-0.1% Tween, BAFF bound to its receptor was detected via its Fc moiety using a peroxidase-conjugated anti-human Fc (Sigma). Absorbance at 450 nm was recorded using an Envision multiwell reader (Perkin Elmer) and IC50 values were calculated by fitting the curves (non-linear regression) using GraphPad Prism®. The results are shown in FIG. 15 and the fitted IC50 values are tabulated below. Results showed that for the selected leads, IC50s were generally lower on BCMA than on TACI (compare FIG. 15A, TACI coating, to FIG. 15B, BCMA coating).

Fitted IC50 Values

|  | A07 | B07 | A05 | B10 | A09 |
|---|---|---|---|---|---|
| BR3 | 6.8 nM | 6.8 nM | 13.8 nM | 2.8 nM | 9.7 nM |
| TAC I | 82.7 nM | 24 nM | 57.8 nM | 14.1 nM | 27.2 nM |
| BCMA | 24.5 nM | 18.9 nM | 17.4 nM | 10.5 nM | 23.6 nM |

Example 10. Anti-BAFF VNAR Inhibition of Splenocyte Proliferation In Vitro

Figure 16:
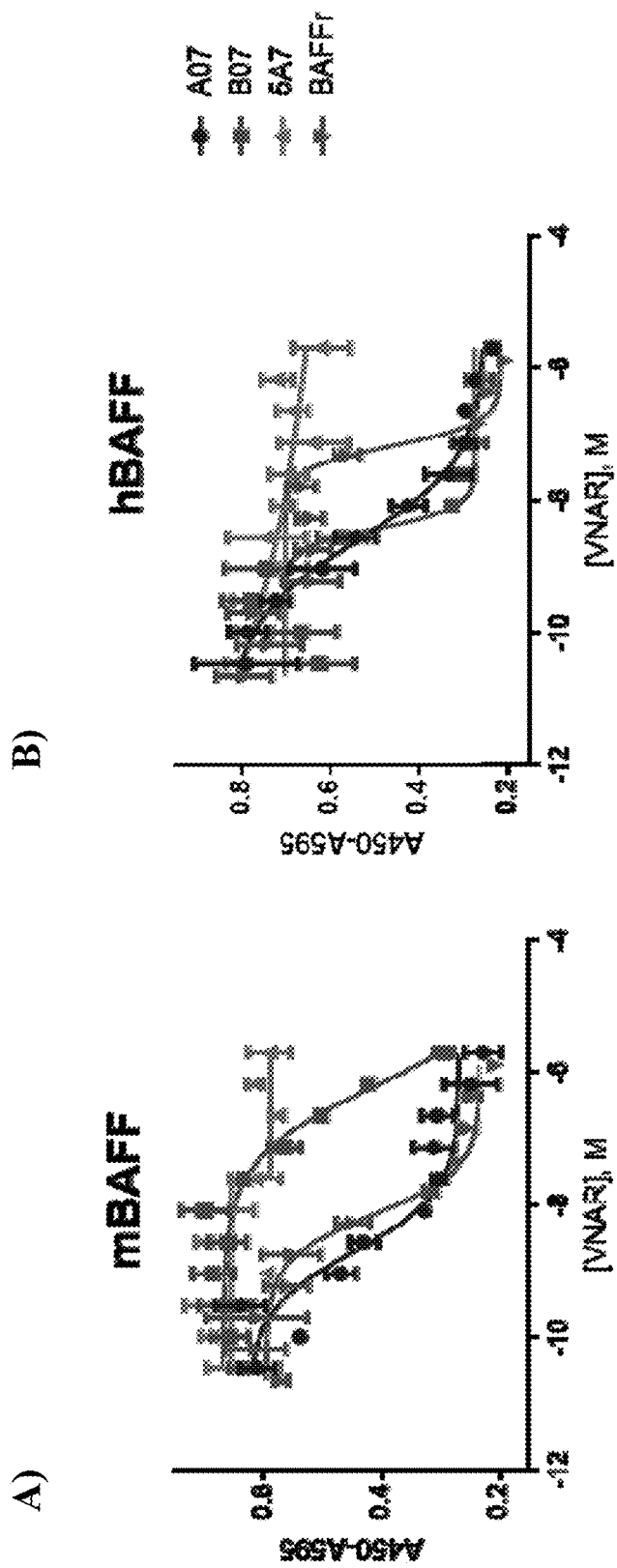
FIGS. 16A-B shows the species cross-reactivity of two VNAR clones (A07, circles; and B07, squares) formatted as a human Fc fusion molecule compared to the positive (BAFFr; downward pointing triangles) and negative (5A7-Fc; upward pointing triangles) controls. A07 and B07 exhibited similar potencies against human BAFF but A07 was more potent in blocking mouse BAFF activity in vitro (see Example 10).

In order to address the species cross-reactivity, the two main lead molecules (A07 and B07) were expressed and purified as a human Fc fusion molecule, together with a negative control anti-lysozyme VNAR (5A7), and tested for their ability to block the proliferation of primary mouse splenic B cells stimulated with either mouse or human recombinant BAFF. Mouse splenocytes were obtained by dissociating spleens of C57BL/6 mice on a 70 µm cell strainer and lysing red blood cell in RBC buffer (Sigma). B cells were then purified by depleting CD43-positive cells using magnetic microbeads (MACS) according to manufacturer's instructions. The obtained B cells were subsequently stimulated with goat anti-mouse IgM antibody (Jackson) at 10 µg/mL final assay concentration. Recombinant VNAR-Fcs were serially-diluted and pre-complexed with recombinant human BAFF-Fc (Sino Biological) at 5 ng/mL final assay concentration, or recombinant mouse BAFF (R&D Systems) at 0.5 ng/mL final assay concentration, in RPMI 1640 supplemented with 10% FBS, for 30 minutes at 37° C. Stimulated B cells were added to the pre-complexed proteins and further incubated for 72 hours at 37° C., 5% CO$_2$. Cell proliferation was then estimated by incubating cells with WST-1 reagent (Roche) and reading absorbance at 450 nM, subtracting a reference wavelength at 595 nM. IC50 values were calculated by fitting the curves (non-linear regression) using GraphPad Prism®. The results are shown in FIG. 16 and the fitted IC50 values are tabulated below.

Fitted IC50 Values

|  | A07 | B07 | 5A7 | BAFFr |
|---|---|---|---|---|
| IC50 (human) | 2.48 nM | 3.79 nM | ~0.0 | 66.2 nM |
| IC50 (mouse) | 1.95 nM | 604 nM | ~0.0 | 7.06 nM |

The results showed that both anti-BAFF VNAR molecules were cross-reacting with human and mouse BAFF. Because A07 has a significantly lower IC50 on mouse BAFF than does B07, it was chosen for subsequent in vivo mouse studies.

Example 11. Effect of Anti-BAFF VNAR-Fc Splenic B Cell Subsets in Mice

Figure 17:
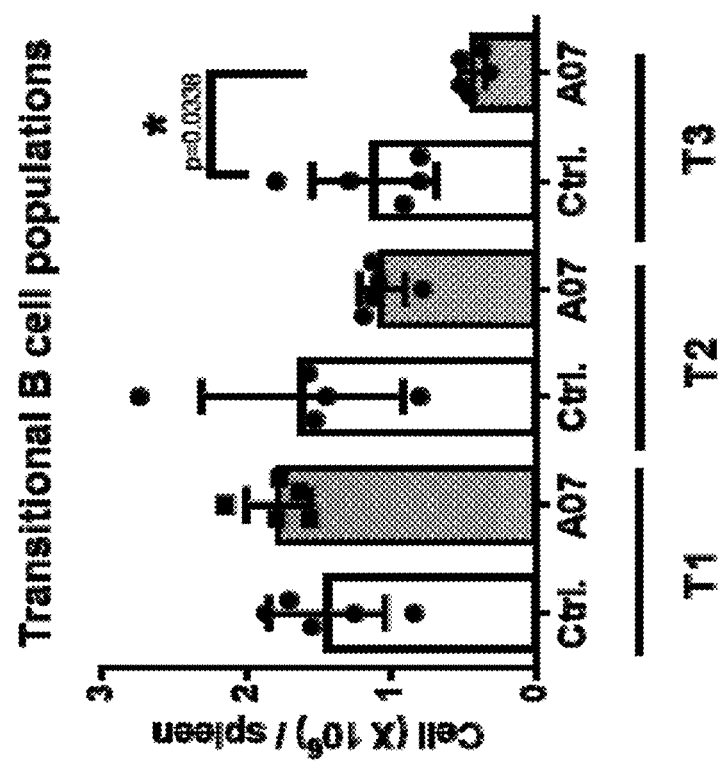
FIG. 17 shows characterization by flow cytometry of the expression of B-cell subset markers on splenocytes isolated from mice injected (i.p.) with 100 µg of A07-Fc at days 0 and 5, and isolated on day 8. Mice treated with A07-Fc (A07) showed a pronounced reduction in the number of late transitional B cells (T3) compared to untreated control mice (Ctrl.) (see Example 11).

To test the effect of anti-BAFF VNAR-Fc molecules on the development of B cells in vivo, 12-week-old female C57BL/6 mice were injected IP with 100 µg of A07-Fc at days 0 and 5. Mice were sacrificed on day 8, spleens were extracted and splenocytes were prepared as single cell suspensions by dispersing the spleens through 100 μM pore size sterile cell strainers in the presence of DNase at 1 μg/mL. Red blood cells were lysed with Red Blood Cell Lysing Buffer (Sigma). The lysis was carried out by adding 1 mL of the lysis buffer to cell pellets formed by centrifugation followed by gentle mixing for 1 minute. The lysis buffer was then neutralized by adding 19 mL RPMI1640 medium containing 2% heat inactivated fetal calf serum (FCS). The remaining cells were centrifuged again at 500 g for 7 minutes and supernatants decanted. The pelleted splenocytes were resuspended in 5 mL of 2% FCS/RPMI1640 medium and passaged through new sterile cell strainers to remove any aggregates and total numbers counted using 0.4% trypan blue. Splenocytes were analysed for total number of B-lymphocytes and subset frequency by flow cytometry using the gating scheme described by Scholz and colleagues (Proc Natl Acad Sci USA. 2008 Oct. 7; 105(40): 15517-22). Immature B cells released from the bone marrow go through transitional stages (classified as T1, T2 & T3 based on the expression of cells surface markers) in the spleen before they develop into mature naïve B cells (Mackay and Schneider Nat Rev Immunol. 2009 July; 9(7):491-502). Results showed that the number of transitional B cells was significantly reduced in mice treated with A07-Fc as compared to untreated mice (FIG. 17). This effect was especially pronounced in late transitional B cells (T3).

Figure 18:
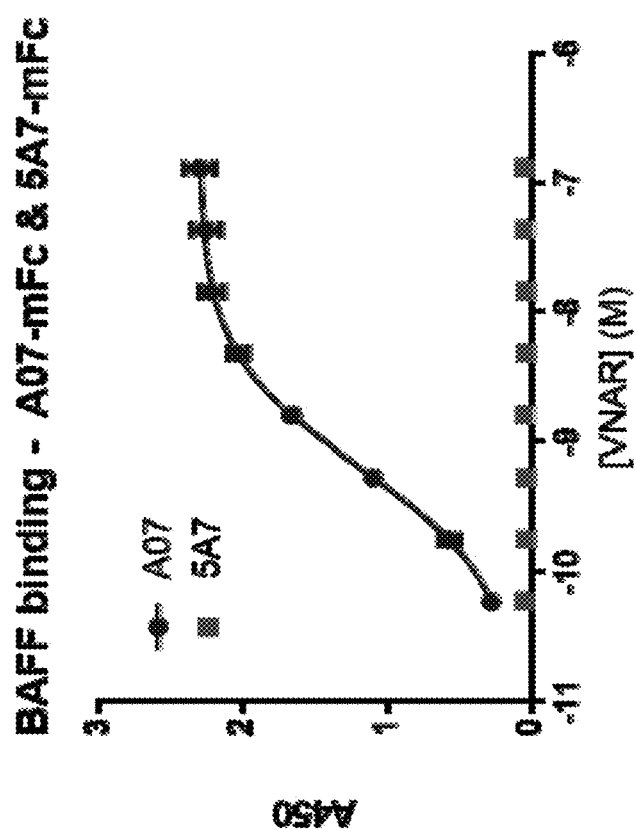
FIG. 18 shows binding potency of anti-BAFF VNAR A07 formatted on a mouse Fc having effector function. The EC50 of A07-mFc was estimated at 0.6 nM based on the ELISA binding curve, whereas the 5A7-mFC control failed to bind BAFF (see Example 12).

Example 12. Effect of Anti-BAFF Formatted on a Mouse Fc Having Effector Function Based on the results of Example 11, the A07 anti-BAFF molecule was reformatted as a mouse Fc fusion protein with effector function intact. The protein was expressed and purified as described above and EC50 binding to human BAFF was assessed by ELISA as previously described. The results are shown in FIG. 18. Results showed that A07-mFc displayed an EC50 of about 0.632 nM, while 5A7 did not bind to BAFF. Mice are then injected i.p. with 100 μg of A07-Fc, 5A7-Fc, or blank control (PBS) on day 0 and again on day 4, 8, and 12 before being culled on day 15. B cell subset populations in the spleen are analysed by flow cytometry as described above and improvements in B cell depletion are anticipated.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

---

What is claimed is:
1. A B-lymphocyte stimulator (BAFF) specific binding moiety in a Type 2 shark VNAR-derived scaffold comprising a CDR1 region and a CDR3 region separated by a framework region,
wherein the CDR1 region comprises or consists essentially of a peptide having an amino acid sequence of formula D-$X_2$-$X_3$-$X_4$-A-L-$X_7$ wherein $X_2$ is N or S; $X_3$ is N, I or S; $X_4$ is C or Y; and $X_7$ is S, P or G (SEQ ID NO: 1);
wherein the CDR3 region comprises a peptide having an amino acid sequence of formula (a) D-$X_a$-L-$Z_{(1-6)}$-C (SEQ ID NO: 2) or formula (b)C-$Z_{(1-6)}$-D-$X_a$-L (SEQ ID NO: 3);
wherein $X_a$ is selected from W, P, R, V or L;
wherein $Z_{(1-6)}$ is a stretch of any one to six amino acid residues, with one Z selected from G, L, F or M; and
wherein said framework region comprises FW2-3 of one of SEQ ID NOS: 4-21.
2. The BAFF specific binding moiety of claim 1, wherein the CDR1 region comprises a peptide selected from DNNCALS (SEQ ID NO: 22), DSNCALS (SEQ ID NO: 23), DSNCALP (SEQ ID NO: 24), or DSICALS (SEQ ID NO: 25.
3. The BAFF specific binding moiety of claim 1, wherein the CDR3 region comprises a peptide selected from DWLLC (SEQ ID NO: 27), DPLLC (SEQ ID NO: 28), DRLLC (SEQ ID NO: 29), DLLLC (SEQ ID NO: 30), DLLFC (SEQ ID NO: 31), DPLFC (SEQ ID NO: 32), DPLMC (SEQ ID NO: 33), DPLTKEC (SEQ ID NO: 34), DPLLFPRDRC (SEQ ID NO: 36) or HGGRSTGLCGDV-LLAGDV (SEQ ID NO: 37).
4. A BAFF antagonist compound comprising a BAFF specific binding moiety of claim 1, wherein the compound competes with BAFF for binding to BAFF receptor.
5. The BAFF antagonist compound of claim 4, wherein the compound binds to human BAFF with an EC50 of at least 300 nM, or of at least 100 nM.
6. A BAFF antagonist compound conjugate comprising (a) a BAFF specific binding moiety of claim 1; and (b) a heterologous compound which differs in biological activity from the binding moiety of (a).
7. The BAFF antagonist compound conjugate of claim 6, wherein the heterologous compound of (b) is a growth factor, cytokine, lymphokine, cell surface antigen or an antibody or antibody fragment which binds to any of the foregoing, a chimeric antigen receptor, a small molecule which is a cytotoxin, a biochemical pathway agonist or antagonist or a diagnostic agent, or a nucleic acid molecule with regulatory properties or which encodes a regulatory molecule in a cell.
8. The BAFF antagonist compound conjugate of claim 7, wherein said diagnostic agent is a fluorescent molecule or other molecular marker.
9. A pharmaceutical composition comprising at least one BAFF specific binding moiety or at least one BAFF antagonist compound of any one of claim 1 or 4, and which optionally further comprises an additional therapeutic agent.
10. A method of producing a BAFF specific binding moiety, or a BAFF antagonist comprising a BAFF specific binding moiety, of any of claim 1 or 4, the method comprising the step of chemically synthesizing one or more of the peptide sequences of SEQ ID NOS: 4-21.

11. A kit for detecting or quantifying BAFF in a sample, the kit comprising at least one BAFF specific binding moiety or antagonist compound of any of claim 1 or 4.
12. A B-lymphocyte stimulator (BAFF) specific binding moiety comprising a Type 2 shark VNAR of the formula
FW1-CDR1-FW2-FW3-CDR3-FW4,
said VNAR comprising any one CDR1 peptide in SEQ ID NOS: 4-21, any one CDR3 peptide in SEQ ID NOS: 4-21 any one FW1 peptide in SEQ ID NOS: 4-21, any one FW2-FW3 peptide in SEQ ID NOS: 4-21 and any one FW4 peptide in SEQ ID NOS: 4-21.
13. The BAFF specific binding moiety of claim 12, wherein the CDR3 region comprises a peptide having an amino acid sequence selected from RRARVIGGEY-CRVQWQDV (SEQ ID NO: 38), LSNVHICCRFGSCADV (SEQ ID NO: 39), APTIISGCSIKRRDV (SEQ ID NO: 40), and TRYVVFSGSTCRMRRADV (SEQ ID NO: 41).
14. The BAFF specific binding moiety of claim 12, wherein said VNAR has an amino acid sequence selected from the group consisting of any one of SEQ ID NOS: 4-21.
15. A variant of a BAFF specific binding moiety of claim 14, wherein the variant differs by 1 to 10 amino acid residues from the recited amino acid sequence and retains BAFF binding activity of at least half of the activity of a non-variant binding moiety.
16. A method to treat a B-cell disease or disorder in a subject which comprises administering a therapeutically-effective amount of a BAFF antagonist compound comprising a BAFF specific binding moiety according to any one of claim 1 or 12, a pharmaceutically acceptable salt or solvate thereof or a composition comprising any of the foregoing, to inhibit or reduce BAFF activity.
17. The method of claim 16, wherein said disease or disorder is associated with a pathology in B cell proliferation, maturation, maintenance or immunoglobulin production; related to a B cell malignancy or is a B-cell related autoimmune condition.
18. The method of claim 17, wherein said disease or condition is Hodgkin's lymphoma (HL), non-Hodgkin's Lymphomas (NHL), diffuse large B cell lymphoma (DLBCL), small lymphocytic lymphoma (SLL), lymphoplasmacytoid lymphoma, lymphoplasmacytic lymphoma (LPL), mantle cell lymphoma (MCL), follicular lymphoma (FL), marginal zone lymphoma (MZL), extranodal mucosa-associated lymphoid tissue lymphoma (MALT lymphoma), nodal monocytoid B-cell lymphoma, splenic diffuse large cell lymphoma, Burkitt's lymphoma, lymphoblastic lymphoma, precursor B lymphoblastic leukemia, B-cell chronic lymphocytic leukemia, chronic lymphocytic leukemia (CLL), acute lymphocytic leukemia (ALL), plasma cell leukemia, solitary plasmacytoma (bone, extramedullary), multiple myeloma (MM), smoldering multiple myeloma (SMM), non-secretory multiple myeloma, POEMS syndrome/osteosclerotic myeloma, monoclonal gammopathy of undetermined significance (MGUS), Waldenstrom's macroglobulinemia, primary amyloidosis (AL), heavy chain disease, type I and II cryoglobulinemia, light chain deposition disease, Goodpasture's syndrome, pemphigus and pemphigoid disorders, epidermolysis bullosa acquisita, systemic lupus erythematosus (SLE), rheumatoid arthritis (RA), multiple sclerosis (MS), idiopathic thrombocytopenic purpura (ITP), Sjogren's syndrome (SS); type 1 or type 2 diabetes, vasculitis, or graft-vs-host or transplant rejection.

* * * * *

SEQUENCE LISTING

```
<160> NUMBER OF SEQ ID NOS: 65

<210> SEQ ID NO 1
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (3)..(3)
<223> OTHER INFORMATION: /replace="Ile" or "Ser"
<220> FEATURE:
<221> NAME/KEY: VARIANT
<222> LOCATION: (4)..(4)
<223> OTHER INFORMATION: /replace="Tyr"
<220> FEATURE:
<221> NAME/KEY: VARIANT
<222> LOCATION: (7)..(7)
<223> OTHER INFORMATION: /replace="Pro" or "Gly"
<220> FEATURE:
<221> NAME/KEY: misc_feature
<222> LOCATION: (1)..(7)
<223> OTHER INFORMATION: /note="Variant residues given in the sequence
      have no preference with respect to those in the annotations
      for variant positions"

<400> SEQUENCE: 1

Asp Asn Asn Cys Ala Leu Ser
1               5

<210> SEQ ID NO 2
<211> LENGTH: 10
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Pro" or "Arg" or "Val" or "Leu"
<220> FEATURE:
<221> NAME/KEY: MOD_RES
<222> LOCATION: (4)..(9)
<223> OTHER INFORMATION: Any amino acid and this region may encompass
      1-6 residues
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 2

Asp Trp Leu Xaa Xaa Xaa Xaa Xaa Xaa Cys
1               5                   10

<210> SEQ ID NO 3
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(7)
<223> OTHER INFORMATION: Any amino acid and this region may encompass
      1-6 residues
<220> FEATURE:
<221> NAME/KEY: VARIANT
<222> LOCATION: (9)..(9)
<223> OTHER INFORMATION: /replace="Pro" or "Arg" or "Val" or "Leu"
<220> FEATURE:
<221> NAME/KEY: misc_feature
<222> LOCATION: (1)..(10)
<223> OTHER INFORMATION: /note="Variant residues given in the sequence
      have no preference with respect to those in the annotations
      for variant positions"

<400> SEQUENCE: 3

Cys Xaa Xaa Xaa Xaa Xaa Xaa Asp Trp Leu
1               5                   10

<210> SEQ ID NO 4
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Asn Asn
            20                  25                  30

Cys Ala Leu Ser Thr Thr Tyr Trp Tyr Arg Lys Lys Ser Gly Ser Thr
        35                  40                  45

Asn Glu Glu Asn Ile Ser Lys Gly Gly Arg Tyr Val Glu Thr Val Asn
    50                  55                  60
```

Ser Gly Ser Lys Ser Phe Ser Leu Arg Ile Asn Asp Leu Thr Val Glu
65                  70                  75                  80

Asp Ser Gly Thr Tyr Arg Cys Lys Val Ser Lys Asp Trp Leu Leu Cys
                85                  90                  95

Arg Asp Arg Gly Arg Arg Glu Thr Asp Val Tyr Gly Asp Gly Thr Ala
            100                 105                 110

Val Thr Val Asn Ala Ala Ser Gly Ala His His His His His Gly
        115                 120                 125

Ala Asp Tyr Lys Asp Asp Asp Lys
        130                 135

<210> SEQ ID NO 5
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
                20                  25                  30

Cys Ala Leu Ser Asn Leu Tyr Trp Tyr Arg Lys Lys Ser Gly Ser Thr
            35                  40                  45

Asn Glu Glu Ser Ile Ser Leu Gly Gly Arg Tyr Val Glu Thr Val Asn
50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Gln Leu Pro Tyr Asp Pro Leu
                85                  90                  95

Thr Lys Glu Cys Ile Leu Gly Arg Met Asp Val Tyr Gly Asp Gly Thr
            100                 105                 110

Ala Val Thr Val Asn Ala Ala Ser Gly Ala His His His His His
        115                 120                 125

Gly Ala Asp Tyr Lys Asp Asp Asp Lys
        130                 135

<210> SEQ ID NO 6
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
                20                  25                  30

Cys Ala Leu Ser Asn Leu Tyr Trp Tyr Arg Lys Lys Ser Gly Ser Thr
            35                  40                  45

Asn Glu Glu Ser Ile Ser Leu Gly Gly Arg Tyr Val Glu Thr Val Asn
50                  55                  60

Ser Gly Ser Lys Ser Phe Ser Leu Arg Ile Asn Asp Leu Thr Val Glu

```
                 65                  70                  75                  80
Asp Ser Gly Thr Tyr Arg Cys Lys Val Arg Ala Arg Val Ile Gly
                 85                  90                  95

Gly Glu Tyr Cys Arg Val Gln Trp Gln Asp Val Tyr Gly Gly Thr
                100                 105                 110

Ala Val Thr Val Asn Ala Ala Ser Gly Ala His His His His His
                115                 120                 125

Gly Ala Asp Tyr Lys Asp Asp Asp Lys
                130                 135

<210> SEQ ID NO 7
<211> LENGTH: 139
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ala Gln Ala Ala Ala Arg Val Asp Gln Thr Pro Gln Thr Ile Thr Lys
1               5                  10                  15

Glu Thr Gly Glu Ser Leu Thr Ile Asn Cys Val Leu Arg Asp Asn Asn
                20                  25                  30

Cys Ala Leu Ser Thr Thr Tyr Trp Tyr Arg Lys Lys Ser Gly Ser Thr
                35                  40                  45

Asn Glu Glu Asn Ile Ser Lys Gly Gly Arg Tyr Val Glu Thr Val Asn
                50                  55                  60

Ser Gly Ser Lys Ser Phe Ser Leu Lys Ile Asn Asp Leu Thr Val Glu
65                  70                  75                  80

Asp Ser Gly Thr Tyr Arg Cys Lys Val Arg Val Asp Arg Leu Leu Cys
                85                  90                  95

Gly Trp Arg Val Gly Arg Arg Gln Leu Gly Asp Val Tyr Gly Gly Gly
                100                 105                 110

Thr Val Val Thr Val Asn Ala Ala Ser Gly Ala His His His His His
                115                 120                 125

His Gly Ala Asp Tyr Lys Asp Asp Asp Lys
                130                 135

<210> SEQ ID NO 8
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Ala Gln Ala Ala Ala Arg Val Asp Gln Thr Pro Gln Thr Ile Thr Lys
1               5                  10                  15

Glu Thr Gly Glu Ser Leu Thr Ile Asn Cys Val Leu Arg Asp Asn Asn
                20                  25                  30

Cys Ala Leu Ser Thr Thr Tyr Trp Tyr Arg Lys Lys Ser Gly Ser Thr
                35                  40                  45

Asn Glu Glu Ser Ile Ser Lys Gly Gly Arg Tyr Val Glu Thr Val Asn
                50                  55                  60

Ser Gly Ser Lys Ser Phe Ser Leu Arg Ile Asn Asp Leu Thr Val Glu
65                  70                  75                  80
```

```
Asp Ser Gly Thr Tyr Arg Cys Lys Val Arg Glu Asp Pro Leu Met Cys
                85                  90                  95

Arg Tyr Tyr Leu Asp Arg Tyr Arg Asp Val Tyr Gly Gly Gly Thr Val
            100                 105                 110

Val Thr Val Asn Ala Ala Ser Gly Ala His His His His His His Gly
        115                 120                 125

Ala Asp Tyr Lys Asp Asp Asp Lys
        130             135

<210> SEQ ID NO 9
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ala Gln Ala Ala Ala Arg Val Asp Gln Thr Pro Arg Ser Val Thr Lys
1               5                   10                  15

Glu Thr Gly Glu Ser Leu Thr Ile Asn Cys Val Leu Arg Asp Ser Ile
            20                  25                  30

Cys Ala Leu Ser Ser Thr His Trp Tyr Arg Lys Lys Ser Gly Ser Thr
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val His Gly Gly Arg Ser Thr Gly
                85                  90                  95

Leu Cys Gly Asp Val Leu Leu Ala Gly Asp Val Tyr Gly Gly Gly Thr
            100                 105                 110

Ala Val Thr Val Asn Ala Ala Ser Gly Ala His His His His His His
        115                 120                 125

Gly Ala Asp Tyr Lys Asp Asp Asp Lys
    130                 135

<210> SEQ ID NO 10
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
            20                  25                  30

Cys Ala Leu Ser Ser Thr Leu Trp Tyr Arg Thr Lys Ser Gly Ser Arg
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Lys Ile Asn Asp Leu Thr Val Glu
65                  70                  75                  80
```

```
Asp Ser Gly Thr Tyr Arg Cys Lys Val Pro Arg Asp Leu Leu Leu Cys
                85                  90                  95

Lys Arg Pro Arg Ala Arg Leu Pro Asp Val Tyr Gly Gly Gly Thr Ala
            100                 105                 110

Val Thr Val Asn Ala Ala Ser Gly Ala His His His His His His Gly
        115                 120                 125

Ala Asp Tyr Lys Asp Asp Asp Lys
    130                 135
```

<210> SEQ ID NO 11
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

```
Ala Gln Ala Ala Ala Arg Val Asp Gln Thr Pro Gln Thr Val Thr Lys
1               5                   10                  15

Glu Thr Gly Glu Ser Leu Thr Ile Asn Cys Val Leu Arg Asp Ala Ser
            20                  25                  30

Tyr Ala Leu Gly Ser Thr Cys Trp Tyr Arg Lys Lys Ser Gly Ser Arg
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Arg Asp Pro Leu Leu Phe Pro
                85                  90                  95

Arg Asp Arg Cys Asp Gly Glu Ser Lys Asp Val Tyr Gly Gly Gly Thr
            100                 105                 110

Val Val Thr Val Asn Ala Ala Ser Gly Ala His His His His His His
        115                 120                 125

Gly Ala Asp Tyr Lys Asp Asp Asp Lys
    130                 135
```

<210> SEQ ID NO 12
<211> LENGTH: 136
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (136)..(136)
<223> OTHER INFORMATION: Any amino acid

<400> SEQUENCE: 12

```
Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
            20                  25                  30

Cys Ala Leu Pro Ser Thr Tyr Trp Tyr Arg Lys Lys Ser Gly Ser Thr
        35                  40                  45

Asn Glu Glu Ser Ile Ser Leu Gly Gly Arg Tyr Val Glu Thr Val Asn
    50                  55                  60
```

```
Ser Gly Ser Lys Ser Phe Ser Leu Arg Ile Asn Asp Leu Thr Val Glu
 65                  70                  75                  80

Asp Ser Gly Thr Tyr Arg Cys Lys Val Leu Ser Asn Val His Ile Cys
                 85                  90                  95

Cys Arg Phe Gly Ser Cys Ala Asp Val Tyr Gly Asp Gly Thr Ala Val
            100                 105                 110

Thr Val Asn Ala Ala Ser Gly Ala His His His His His Gly Ala
        115                 120                 125

Asp Tyr Lys Asp Asp Asp Xaa
        130             135

<210> SEQ ID NO 13
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ala Gln Ala Ala Ala Arg Val Asp Gln Thr Pro Arg Ser Val Thr Lys
 1               5                  10                  15

Glu Thr Gly Glu Ser Leu Thr Ile Asn Cys Val Leu Arg Asp Ser Asn
                20                  25                  30

Cys Ala Leu Ser Ser Thr Tyr Trp Tyr Arg Lys Lys Ser Gly Ser Thr
            35                  40                  45

Asn Glu Glu Asn Ile Ser Lys Gly Gly Arg Tyr Val Glu Thr Val Asn
 50                  55                  60

Ser Gly Ser Lys Ser Phe Ser Leu Arg Ile Asn Asp Leu Thr Val Glu
 65                  70                  75                  80

Asp Ser Gly Thr Tyr Arg Cys Lys Val Met Leu Asp Pro Leu Leu Cys
                 85                  90                  95

Pro Ala Leu Leu Glu Ser Met Thr Asp Val Tyr Gly Gly Gly Thr Ala
            100                 105                 110

Val Thr Val Asn Ala Ala Ser Gly Ala His His His His His Gly
        115                 120                 125

Ala Asp Tyr Lys Asp Asp Asp Lys
        130             135

<210> SEQ ID NO 14
<211> LENGTH: 135
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ala Gln Ala Ala Ala Arg Val Asp Gln Thr Pro Gln Thr Ile Thr Lys
 1               5                  10                  15

Glu Thr Gly Glu Ser Leu Thr Ile Asn Cys Val Leu Arg Asp Ser Asn
                20                  25                  30

Cys Ala Leu Ser Ser Thr Tyr Trp Tyr Arg Lys Lys Ser Gly Ser Thr
            35                  40                  45

Asn Glu Glu Ser Ile Ser Lys Gly Gly Arg Tyr Val Glu Thr Val Asn
 50                  55                  60

Ser Gly Ser Lys Ser Phe Ser Leu Arg Ile Asn Asp Leu Thr Val Glu
```

```
                65                  70                  75                  80
Asp Ser Gly Thr Tyr Arg Cys Asn Val Ala Pro Thr Ile Ile Ser Gly
                    85                  90                  95

Cys Ser Ile Lys Arg Arg Asp Val Tyr Gly Gly Thr Ala Val Thr
            100                 105                 110

Val Asn Ala Ala Ser Gly Ala His His His His His Gly Ala Asp
        115                 120                 125

Tyr Lys Asp Asp Asp Asp Lys
    130                 135

<210> SEQ ID NO 15
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
            20                  25                  30

Cys Ala Leu Ser Ser Thr Tyr Trp Tyr Arg Lys Lys Ser Gly Ser Thr
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Arg Ile Asp Pro Leu Leu Cys
                    85                  90                  95

Asn Ala Ser Tyr Val Lys Trp Asp Asp Val Tyr Gly Gly Thr Val
            100                 105                 110

Val Thr Val Asn Ala Ala Ser Gly Ala His His His His His Gly
        115                 120                 125

Ala Asp Tyr Lys Asp Asp Asp Lys
    130                 135

<210> SEQ ID NO 16
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Ala Gln Ala Ala Ala Arg Val Asp Gln Thr Pro Arg Ser Val Thr Lys
1               5                   10                  15

Glu Thr Gly Glu Ser Leu Thr Ile Asn Cys Val Leu Arg Asp Ser Ile
            20                  25                  30

Cys Ala Leu Ser Ser Thr His Trp Tyr Arg Lys Lys Ser Gly Ser Thr
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80
```

```
Asp Ser Gly Thr Tyr Arg Cys Lys Val Asn His Asp Leu Leu Thr Ser
                85                  90                  95

Ser Arg Arg Cys Gln Ser Gln Ile Lys Asp Val Tyr Gly Gly Gly Thr
            100                 105                 110

Val Val Thr Val Asn Ala Ala Ser Gly Ala His His His His His His
        115                 120                 125

Gly Ala Asp Tyr Lys Asp Asp Asp Lys
    130                 135
```

<210> SEQ ID NO 17
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Ala Gln Ala Ala Ala Arg Val Asp Gln Thr Pro Arg Ser Val Thr Lys
1               5                   10                  15

Glu Thr Gly Glu Ser Leu Thr Ile Asn Cys Val Leu Arg Asp Asn Asn
            20                  25                  30

Cys Ala Leu Ser Thr Thr Tyr Trp Tyr Arg Lys Lys Ser Gly Ser Thr
        35                  40                  45

Asn Glu Glu Asn Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Lys Pro Asp Leu Leu Phe Cys
                85                  90                  95

Ser Ser Ser Gly Leu Gly Leu Ile Gln Asp Val Tyr Gly Gly Gly Thr
            100                 105                 110

Ala Val Thr Val Asn Ala Ala Ser Gly Ala His His His His His His
        115                 120                 125

Gly Ala Asp Tyr Lys Asp Asp Asp Lys
    130                 135
```

<210> SEQ ID NO 18
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

```
Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Ser Asn
            20                  25                  30

Cys Ala Leu Ser Ser Thr Tyr Trp Tyr Arg Lys Lys Ser Gly Ser Thr
        35                  40                  45

Asn Glu Glu Ser Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80
```

```
Asp Ser Gly Thr Tyr Arg Cys Lys Val Phe Ile Asp Pro Leu Leu Cys
            85                  90                  95

Ser Arg Asp Ala Leu Gly Phe Ser Asp Val Tyr Gly Asp Gly Thr Ala
            100                 105                 110

Val Thr Val Asn Ala Ala Ser Gly Ala His His His His His His Gly
        115                 120                 125

Ala Asp Tyr Lys Asp Asp Asp Asp Lys
    130                 135

<210> SEQ ID NO 19
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Asn Asn
            20                  25                  30

Cys Ala Leu Ser Thr Thr Tyr Trp Tyr Arg Lys Lys Ser Gly Ser Thr
        35                  40                  45

Asn Glu Glu Asn Ile Ser Lys Gly Gly Arg Tyr Val Glu Thr Val Asn
    50                  55                  60

Ser Gly Ser Lys Ser Phe Ser Leu Lys Ile Asn Asp Leu Thr Val Lys
65                  70                  75                  80

Asp Ser Gly Thr Tyr Arg Cys Lys Val Thr Arg Asp Pro Leu Phe Cys
            85                  90                  95

Ser Tyr Arg Ala Ser Lys Arg His Asp Val Tyr Gly Gly Thr Val
            100                 105                 110

Val Thr Val Asn Ala Ala Ser Gly Ala His His His His His His Gly
        115                 120                 125

Ala Asp Tyr Lys Asp Asp Asp Asp Lys
    130                 135

<210> SEQ ID NO 20
<211> LENGTH: 137
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Gln Ala Ala Ala Arg Val Asp Gln Thr Pro Gln Thr Ile Thr Lys
1               5                   10                  15

Glu Thr Gly Glu Ser Leu Thr Ile Asn Cys Val Leu Arg Asp Asn Asn
            20                  25                  30

Cys Ala Leu Ser Thr Thr Tyr Trp Tyr Arg Lys Lys Ser Gly Ser Thr
        35                  40                  45

Asn Glu Glu Asn Ile Ser Lys Gly Gly Arg Tyr Val Glu Thr Val Asn
    50                  55                  60

Ser Gly Ser Lys Ser Phe Ser Leu Arg Ile Asn Asp Leu Thr Val Glu
65                  70                  75                  80

Asp Ser Gly Thr Tyr Arg Cys Lys Val Arg Leu Asp Leu Leu Leu Cys
```

```
                    85                  90                  95
Arg Asn Gly Ser Thr Asn Ser Ile Asp Val Tyr Gly Gly Thr Ala
                100                 105                 110

Val Thr Val Asn Ala Ala Ser Gly Ala His His His His His Gly
            115                 120                 125

Ala Asp Tyr Lys Asp Asp Asp Lys
    130                 135
```

```
<210> SEQ ID NO 21
<211> LENGTH: 138
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Gln Ala Ala Ala Arg Val Asp Gln Thr Pro Arg Ser Val Thr Lys
1               5                   10                  15

Glu Thr Gly Glu Ser Leu Thr Ile Asn Cys Val Leu Arg Asp Ser Ile
                20                  25                  30

Cys Ala Leu Ser Ser Thr His Trp Tyr Arg Lys Lys Ser Gly Ser Thr
            35                  40                  45

Asn Glu Glu Ser Ile Ser Leu Gly Gly Arg Tyr Val Glu Thr Val Asn
50                  55                  60

Ser Gly Ser Lys Ser Phe Ser Leu Lys Ile Asn Asp Leu Thr Val Glu
65                  70                  75                  80

Asp Ser Gly Thr Tyr Arg Cys Lys Val Thr Arg Tyr Val Val Phe Ser
                85                  90                  95

Gly Ser Thr Cys Arg Met Arg Arg Ala Asp Val Tyr Gly Gly Gly Thr
                100                 105                 110

Val Val Thr Met Asn Ala Ala Ser Gly Ala His His His His His
            115                 120                 125

Gly Ala Asp Tyr Lys Asp Asp Asp Lys
    130                 135
```

```
<210> SEQ ID NO 22
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Asp Asn Asn Cys Ala Leu Ser
1               5
```

```
<210> SEQ ID NO 23
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Asp Ser Asn Cys Ala Leu Ser
1               5
```

```
<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Asp Ser Asn Cys Ala Leu Pro
1               5

<210> SEQ ID NO 25
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Asp Ser Ile Cys Ala Leu Ser
1               5

<210> SEQ ID NO 26
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Asp Ala Ser Tyr Ala Leu Gly
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Asp Trp Leu Leu Cys
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Asp Pro Leu Leu Cys
1               5

<210> SEQ ID NO 29
<211> LENGTH: 5
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Asp Arg Leu Leu Cys
1               5

<210> SEQ ID NO 30
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Asp Leu Leu Leu Cys
1               5

<210> SEQ ID NO 31
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asp Leu Leu Phe Cys
1               5

<210> SEQ ID NO 32
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asp Pro Leu Phe Cys
1               5

<210> SEQ ID NO 33
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Asp Pro Leu Met Cys
1               5

<210> SEQ ID NO 34
<211> LENGTH: 7
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 34

Asp Pro Leu Thr Lys Glu Cys
1               5

<210> SEQ ID NO 35
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Asp Leu Leu Thr Ser Ser Arg Arg Cys
1               5

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Asp Pro Leu Leu Phe Pro Arg Asp Arg Cys
1               5                   10

<210> SEQ ID NO 37
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

His Gly Gly Arg Ser Thr Gly Leu Cys Gly Asp Val Leu Leu Ala Gly
1               5                   10                  15

Asp Val

<210> SEQ ID NO 38
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Arg Arg Ala Arg Val Ile Gly Gly Glu Tyr Cys Arg Val Gln Trp Gln
1               5                   10                  15

Asp Val

<210> SEQ ID NO 39
<211> LENGTH: 16
<212> TYPE: PRT
<213> ORGANISM: Artificial Sequence
<220> FEATURE:
<221> NAME/KEY: source
```

-continued

<223> OTHER INFORMATION: /note="Description of Artificial Sequence:
      Synthetic peptide"

<400> SEQUENCE: 39

Leu Ser Asn Val His Ile Cys Cys Arg Phe Gly Ser Cys Ala Asp Val
1               5                   10                  15

<210> SEQ ID NO 40
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ala Pro Thr Ile Ile Ser Gly Cys Ser Ile Lys Arg Arg Asp Val
1               5                   10                  15

<210> SEQ ID NO 41
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Thr Arg Tyr Val Val Phe Ser Gly Ser Thr Cys Arg Met Arg Arg Ala
1               5                   10                  15

Asp Val

<210> SEQ ID NO 42
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 42

His His His His His His
1               5

<210> SEQ ID NO 43
<211> LENGTH: 99
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

```
Ser Phe Ser Leu Arg Ile Asn Asp Leu Thr Val Glu Asp Ser Gly Thr
 65                  70                  75                  80

Tyr Arg Cys Asn Val Tyr Gly Gly Thr Ala Val Thr Val Asn Ala
                 85                  90                  95

Ala Ser Gly
```

<210> SEQ ID NO 44
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Pro Pro Ala Gly Arg Tyr Glu His Cys Asp Trp
                 85                  90                  95

Thr Gly Val Tyr Gly Gly Thr Val Val Thr Val Asn Ala Ala Ser
            100                 105                 110

Gly
```

<210> SEQ ID NO 45
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

```
Ala Arg Val Asp Gln Thr Pro Gln Thr Ile Thr Lys Glu Thr Gly Glu
  1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Asp Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Trp Lys Lys Ala Gly Met Ile Gly Tyr Asp Cys
                 85                  90                  95

Gly Leu Gln Ala Arg Asp Val Tyr Gly Gly Thr Val Val Thr Val
            100                 105                 110

Asn Ala Ala Ser Gly
            115
```

```
<210> SEQ ID NO 46
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Pro Thr Trp Ser Asp Cys Leu Asn Arg
                85                  90                  95

Asp Val Tyr Gly Asp Gly Thr Ala Val Thr Val Asn Ala Ala Ser Gly
            100                 105                 110

<210> SEQ ID NO 47
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Gly Arg Gly Arg Ile Thr His Asp Cys Thr Gly Val
                85                  90                  95

Lys Tyr Asp Val Tyr Gly Gly Gly Thr Val Val Thr Val Asn Ala Ala
            100                 105                 110

Ser Gly

<210> SEQ ID NO 48
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48
```

```
Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Lys Ile Asn Asp Leu Thr Val Glu Asp Ser Gly Thr
65                  70                  75                  80

Tyr Arg Cys Lys Ala Gln Gln Gly Gly Leu Cys Trp Gly Ser Lys Ser
                85                  90                  95

Asp Val Tyr Gly Gly Gly Thr Val Thr Val Asn Ala Ala Ser Gly
                100                 105                 110
```

<210> SEQ ID NO 49  
<211> LENGTH: 110  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 49

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
                20                  25                  30

Ser Thr Tyr Trp Tyr Arg Lys Lys Ser Gly Ser Thr Asn Glu Ala Arg
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Gly Lys Leu Val Trp Leu Tyr Asp Cys Pro Asp Val
                85                  90                  95

Tyr Gly Asp Gly Thr Ala Val Thr Val Asn Ala Ala Ser Gly
                100                 105                 110
```

<210> SEQ ID NO 50  
<211> LENGTH: 114  
<212> TYPE: PRT  
<213> ORGANISM: Artificial Sequence  
<220> FEATURE:  
<221> NAME/KEY: source  
<223> OTHER INFORMATION: /note="Description of Artificial Sequence: Synthetic polypeptide"

<400> SEQUENCE: 50

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
                20                  25                  30

Thr Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
        50                  55                  60
```

```
Ser Phe Ser Leu Lys Ile Asn Asp Leu Thr Val Glu Asp Ser Gly Thr
 65                  70                  75                  80

Tyr Arg Cys Asn Val Arg Leu Ala Gly Met Trp Ile Cys Leu Asn Trp
                 85                  90                  95

Tyr Asp Ala Asp Tyr Gly Gly Gly Thr Ala Val Thr Val Asn Ala Ala
                100                 105                 110

Ser Gly

<210> SEQ ID NO 51
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Lys Val Arg Pro Leu Leu Pro Tyr Gly Gly Tyr Asp Cys
                 85                  90                  95

Ala Val Leu Gly Glu Glu Ile Tyr Gly Asp Gly Thr Val Thr Val
                100                 105                 110

Asn Ala Ala Ser Gly
            115

<210> SEQ ID NO 52
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Leu Trp Gly Trp Tyr Asp Cys Ala Leu Gly Ala Asn
                 85                  90                  95

Tyr Asp Val Tyr Gly Gly Gly Thr Val Val Thr Val Asn Ala Ala Ser
                100                 105                 110
```

Gly

<210> SEQ ID NO 53
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 53

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Tyr Gly Met Ser Ile Tyr Gly Asn Trp Cys Asp
                85                  90                  95

Val Asn Tyr Gly Gly Gly Thr Val Thr Val Asn Ala Ala Ser Gly
            100                 105                 110
```

<210> SEQ ID NO 54
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (7)..(7)
<223> OTHER INFORMATION: /replace="Lys"
<220> FEATURE:
<221> NAME/KEY: misc_feature
<222> LOCATION: (1)..(8)
<223> OTHER INFORMATION: /note="Variant residues given in the sequence have no preference with respect to those in the annotations for variant positions"

<400> SEQUENCE: 54

```
Ser Gly Thr Tyr Arg Cys Asn Val
1               5
```

<210> SEQ ID NO 55
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:

<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other

<400> SEQUENCE: 55
nnknnknnkn nktgcnnknn knnknnk                                27

<210> SEQ ID NO 56
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other

<400> SEQUENCE: 56
nnknnknnkd rydrydrynn knnknnk                                27

<210> SEQ ID NO 57
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asp Val Tyr Gly Gly Gly Thr Val Val Thr Val Asn Ala

<210> SEQ ID NO 58
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asp Val Tyr Gly Gly Gly Thr Ala Val Thr Val Asn Ala
1               5                   10

<210> SEQ ID NO 59
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Asp Val Tyr Gly Asp Gly Thr Ala Val Thr Val Asn Ala
1               5                   10

<210> SEQ ID NO 60
<211> LENGTH: 131
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Gln Ala Ala Ala Arg Val Asp Gln Thr Pro Arg Ser Val Thr Lys Glu
1               5                   10                  15

Thr Gly Glu Ser Leu Thr Ile Asn Cys Val Leu Arg Asp Ala Ser Tyr
            20                  25                  30

Ala Leu Gly Ser Thr Cys Trp Tyr Arg Lys Lys Ser Gly Ser Thr Asn
        35                  40                  45

Glu Glu Ser Ile Ser Lys Gly Gly Arg Tyr Val Glu Thr Val Asn Ser
    50                  55                  60

Gly Ser Lys Ser Phe Ser Leu Arg Ile Asn Asp Leu Thr Val Glu Asp
65                  70                  75                  80

Gly Gly Thr Tyr Arg Cys Gly Val Cys Arg Gly Ile Tyr Ser Arg Gly
                85                  90                  95

Tyr Ser Trp Cys Asp Trp Arg Tyr Gln Ser His Ala Asp Val Leu Leu
            100                 105                 110

Ile Gly Val Ser Gln Asn Ala Ala Cys Gly Asp Gly Thr Ala Val Thr
        115                 120                 125

Val Asn Ala
    130

<210> SEQ ID NO 61
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic polypeptide"

<400> SEQUENCE: 61

Gln Ala Ala Ala Arg Val Asp Gln Thr Pro Arg Ser Val Thr Lys Glu
1               5                   10                  15

Thr Gly Glu Ser Leu Thr Ile Asn Cys Val Leu Arg Asp Ala Ser Tyr
            20                  25                  30

Glu Leu Gly Ser Thr Cys Trp Tyr Arg Lys Lys Ser Gly Ser Thr Asn
        35                  40                  45

Glu Glu Ser Ile Ser Lys Gly Gly Arg Tyr Val Glu Thr Val Asn Ser
    50                  55                  60

Gly Ser Lys Ser Phe Ser Leu Arg Ile Asn Asp Leu Thr Val Glu Asp
65                  70                  75                  80

Gly Gly Thr Tyr Arg Cys Gly Ala Ala Thr Arg Ala Gly Pro Arg Glu
                85                  90                  95

Ser Cys Asp Tyr Lys Gly Gly Ser Cys Ala Pro Pro Met Ala Tyr
            100                 105                 110

Ala Ala Cys Gly Asp Gly Thr Ala Val Thr Val Asn Ala
        115                 120                 125

<210> SEQ ID NO 62
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Ala Ala Ala Arg Val Asp Gln Thr Pro Arg Ser Val Thr Lys Glu
1               5                   10                  15

Thr Gly Glu Ser Leu Thr Ile Asn Cys Val Leu Arg Asp Ala Ser Tyr
            20                  25                  30

Ala Leu Gly Ser Thr Cys Trp Tyr Arg Lys Lys Ser Gly Ser Thr Asn
        35                  40                  45

Glu Glu Ser Ile Ser Lys Gly Gly Arg Tyr Val Glu Thr Val Asn Ser
    50                  55                  60

Gly Ser Lys Ser Phe Ser Leu Arg Ile Asn Asp Leu Thr Val Glu Asp
65                  70                  75                  80

Gly Gly Thr Tyr Arg Cys Gly Val Met Ala Gly Val Asp Arg Ser Lys
                85                  90                  95

Tyr Ser Cys Asp Tyr Glu Arg Pro Arg Ala Leu Cys Ser Phe His Ile
            100                 105                 110

Ala Ala Cys Gly Asp Gly Thr Ala Val Thr Val Asn Ala
        115                 120                 125

<210> SEQ ID NO 63
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (2)..(11)

```
<223> OTHER INFORMATION: Any amino acid
<220> FEATURE:
<221> NAME/KEY: MOD_RES
<222> LOCATION: (14)..(30)
<223> OTHER INFORMATION: Any amino acid

<400> SEQUENCE: 63

Cys Xaa Xaa Xaa Xaa Xaa Xaa Xaa Xaa Xaa Cys Asp Xaa Xaa Xaa
1               5                   10                  15

Xaa Xaa Xaa Xaa Xaa Xaa Xaa Xaa Xaa Xaa Xaa Xaa Xaa Ala Ala
            20                  25                  30

<210> SEQ ID NO 64
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(9)
<223> OTHER INFORMATION: Any amino acid
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (18)..(24)
<223> OTHER INFORMATION: Any amino acid

<400> SEQUENCE: 64

Xaa Xaa Xaa Xaa Xaa Xaa Xaa Xaa Xaa Cys Asp Xaa Xaa Xaa Xaa
1               5                   10                  15

Cys Xaa Xaa Xaa Xaa Xaa Xaa Xaa Ala Ala
            20                  25

<210> SEQ ID NO 65
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(10)
<223> OTHER INFORMATION: Any amino acid
<220> FEATURE:
<221> NAME/KEY: MOD_RES
<222> LOCATION: (13)..(19)
<223> OTHER INFORMATION: Any amino acid
<220> FEATURE:
<221> NAME/KEY: MOD_RES
<222> LOCATION: (21)..(24)
<223> OTHER INFORMATION: Any amino acid

<400> SEQUENCE: 65

Xaa Xaa Xaa Xaa Xaa Xaa Xaa Xaa Xaa Xaa Cys Asp Xaa Xaa Xaa
1               5                   10                  15

Xaa Xaa Xaa Xaa Cys Xaa Xaa Xaa Xaa Ala Ala
            20                  25
```